(12) United States Patent
Neal, II et al.

(10) Patent No.: US 12,691,281 B2
(45) Date of Patent: Jul. 28, 2026

(54) INDUCED EXTRAVASATION BY ENERGY DELIVERY TO TISSUE

(71) Applicant: Galvanize Therapeutics, Inc., Redwood City, CA (US)

(72) Inventors: Robert E. Neal, II, Redwood City, CA (US); Timothy J. O'Brien, Redwood City, CA (US); Chiara Pastori, Redwood City, CA (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 83 days.

(21) Appl. No.: 18/534,287

(22) Filed: Dec. 8, 2023

(65) Prior Publication Data

US 2024/0173557 A1 May 30, 2024

Related U.S. Application Data

(63) Continuation of application No. PCT/US2022/015217, filed on Feb. 4, 2022, which is
(Continued)

(51) Int. Cl.
| | |
|---|---|
| *A61N 1/32* | (2006.01) |
| *A61N 1/36* | (2006.01) |
| *A61N 1/40* | (2006.01) |

(52) U.S. Cl.
CPC ........... *A61N 1/327* (2013.01); *A61N 1/3603* (2017.08); *A61N 1/40* (2013.01)

(58) Field of Classification Search
CPC ......... A61N 1/327; A61N 1/3603; A61N 1/40
(Continued)

(56) References Cited

U.S. PATENT DOCUMENTS

| | | | | |
|---|---|---|---|---|
| 5,386,837 A | * | 2/1995 | Sterzer | .............. A61M 37/0092 |
| | | | | 128/898 |
| 2005/0096584 A1 | | 5/2005 | Ferek-petric | |
| | | (Continued) | | |

FOREIGN PATENT DOCUMENTS

| | | |
|---|---|---|
| JP | 2018-532403 A | 11/2018 |
| JP | 2019-524396 A | 9/2019 |
| | (Continued) | |

OTHER PUBLICATIONS

Extended European Search Report for European Patent Application No. 22820712.2, Applicant: Galvanize Therapeutics, Inc., mailed Apr. 7, 2025, 9 pages.

(Continued)

*Primary Examiner* — Nadia A Mahmood
(74) *Attorney, Agent, or Firm* — PERKINS COIE LLP

(57) ABSTRACT

Devices, systems and methods are provided for treating of target tissue within a body of a patient, particularly tumors. Such systems can include an energy delivery device having at least one energy delivery body configured to be positioned near a target tissue area of the patient, and a generator in electrical communication with the at least one energy body. The generator can include at least one energy delivery algorithm configured to provide an electric signal of pulsed electric field energy deliverable to the at least one energy delivery body so as to induce extravasation within the target tissue area.

26 Claims, 17 Drawing Sheets

Related U.S. Application Data a continuation-in-part of application No. PCT/US2021/044469, filed on Aug. 4, 2021.

(60) Provisional application No. 63/209,335, filed on Jun. 10, 2021, provisional application No. 63/061,114, filed on Aug. 4, 2020, provisional application No. 63/061,091, filed on Aug. 4, 2020.

(58) Field of Classification Search
USPC .......................................................... 607/2
See application file for complete search history.

(56) References Cited

U.S. PATENT DOCUMENTS

| | | |
|---|---|---|
| 2005/0170510 A1 | 8/2005 | Huang et al. |
| 2007/0191904 A1 | 8/2007 | Libbus et al. |
| 2016/0287314 A1 | 10/2016 | Arena et al. |
| 2017/0087224 A1 | 3/2017 | Quake |
| 2018/0311497 A1 | 11/2018 | Viswanathan et al. |
| 2019/0201089 A1 | 7/2019 | Waldstreicher et al. |
| 2019/0269826 A1 | 9/2019 | Peyman |
| 2023/0405313 A1 | 12/2023 | Pastori et al. |

FOREIGN PATENT DOCUMENTS

| | | |
|---|---|---|
| JP | 2019-530529 A | 10/2019 |
| JP | 2021-508533 A | 3/2021 |
| WO | 0155294 | 8/2001 |
| WO | 2017173089 A1 | 10/2017 |
| WO | 2019133608 A1 | 7/2019 |
| WO | 2020096836 A2 | 5/2020 |
| WO | 2020118383 | 6/2020 |
| WO | 2021011733 A1 | 1/2021 |
| WO | 2022031797 | 2/2022 |

OTHER PUBLICATIONS

International Search Report and Written Opinion mailed May 6, 2022 for International Patent Application No. PCT/US22/15217.
International Search Report and Written Opinion mailed Nov. 8, 2021 for International Patent Application No. PCT/US21/44469.
Extended European Search Report for European Patent Application No. 21853941.9, Applicant: Galvanize Therapeutics, Inc., mailed Jul. 23, 2024, 7 pages.

* cited by examiner

Pulmonary artery distribution

FIG. 8A                    FIG. 8B

INDUCED EXTRAVASATION BY ENERGY DELIVERY TO TISSUE

CROSS REFERENCE TO RELATED APPLICATIONS

This application is a continuation of International Patent Application No. PCT/US2022/015217, filed Feb. 4, 2022, which claims priority to and the benefit of U.S. Provisional Patent Application No. 63/209,335, filed Jun. 10, 2021, entitled "Induced Extravasation by Energy Delivery to Tissue", and is a U.S. continuation-in-part of PCT/US2021/044469, filed on Aug. 4, 2021, entitled "PULSED ELECTRIC FIELD TRANSFER OF MOLECULES TO CELLS WHILE IN THE BODY" which claims priority to and the benefit of U.S. Provisional Patent Application No. 63/061,114, filed Aug. 4, 2020, entitled "Enhanced Transfer with Pulsed Electric Fields", U.S. Provisional Patent Application No. 63/061,091, filed Aug. 4, 2020, entitled "Pulsed Electric Fields in the Eye", and U.S. Provisional Patent Application No. 63/209,335, filed Jun. 10, 2021, entitled "Induced Extravasation by Energy Delivery to Tissue", the disclosures of all of the foregoing applications are incorporated herein by reference in their entireties.

BACKGROUND

Cells in the body regularly die off and new cells divide and replace them when this happens. However, when cells divide uncontrollably and serve no purpose, a mass of tissue known as a tumor can appear. Tumors are groups of abnormal cells that form growths or lumps. They can start in any one of the many cells throughout the body. Tumors grow and behave differently, depending on whether they are cancerous (malignant), non-cancerous (benign) or precancerous. Malignant tumors grow beyond their usual boundaries to invade adjoining parts of the body and/or spread to other organs. The latter process is called metastasizing and is a major cause of death from cancer. A neoplasm and malignant tumor are common names for cancer.

There are many types of cancer treatment. The types of treatment received will depend on the type of cancer and how advanced it is. Some people with cancer will have only one type of treatment. But most people have a combination of treatments, such as surgery with chemotherapy and radiation therapy. Chemotherapy is a type of cancer treatment that uses chemotherapeutic agents as part of a standardized chemotherapy regimen. Chemotherapy may be given with a curative intent or it may aim to prolong life or to reduce symptoms. Chemotherapy is one of the major categories of the medical discipline specifically devoted to pharmacotherapy for cancer, which is called medical oncology.

Traditional chemotherapeutic agents are cytotoxic by means of interfering with cell division (mitosis) but cancer cells vary widely in their susceptibility to these agents. To a large extent, chemotherapy can be thought of as a way to damage or stress cells, which may then lead to cell death if apoptosis is initiated. Many of the side effects of chemotherapy can be traced to damage to normal cells that divide rapidly and are thus sensitive to anti-mitotic drugs: cells in the bone marrow, digestive tract and hair follicles. This results in the most common side-effects of chemotherapy: myelosuppression (decreased production of blood cells, hence also immunosuppression), mucositis (inflammation of the lining of the digestive tract), and alopecia (hair loss). Because of the effect on immune cells (especially lymphocytes), chemotherapy drugs often find use in a host of diseases that result from harmful overactivity of the immune system against self (so-called autoimmunity). These include rheumatoid arthritis, systemic lupus erythematosus, multiple sclerosis, vasculitis and many others.

The development of therapies with specific molecular or genetic targets, which inhibit growth-promoting signals from classic endocrine hormones (primarily estrogens for breast cancer and androgens for prostate cancer) are now called hormonal therapies. By contrast, other inhibitions of growth-signals like those associated with receptor tyrosine kinases are referred to as targeted therapy. The use of drugs (whether chemotherapy, hormonal therapy or targeted therapy) typically constitutes systemic therapy for cancer in that they are introduced into the blood stream and are therefore in principle able to address cancer at any anatomic location in the body. Systemic therapy is often used in conjunction with other modalities that constitute local therapy (i.e. treatments whose efficacy is confined to the anatomic area where they are applied) for cancer such as radiation therapy, surgery or hyperthermia therapy.

Systemic therapy has an important role in the management of patients diagnosed with cancer, but the use of many of these agents is clearly associated with long-term toxicities in long-term survivors. Present and future challenges include appropriate delivery of cytotoxic agents (and other components of multimodal anti-cancer treatment regimens) to maximize therapeutic efficacy while limiting both acute and long-term side-effects. The sequential use of several different chemotherapy agents is becoming increasingly common to overcome tumor resistance as it emerges e.g., in patients with metastatic colon and breast cancer, and there is evidence for improved overall survival. Nevertheless, these patients often accumulate considerable exposure to multiple chemotherapeutic agents and are thus at high risk of cumulative treatment-related side-effects. Paradoxically patient ability or willingness to tolerate such side-effects, rather than uncontrolled disease, or absence of potential active anti-cancer treatments, may rapidly become the limiting factor for treatment success in this population.

Thus, improvements in therapy for cancer and other tumors are desired. Such treatments should be safe, effective, and lead to reduced complications. Such treatments should also be applicable to therapies involving transfer of various types of molecules to cells, particularly macromolecules. At least some of these objectives will be met by the systems, devices and methods described herein.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8A illustrates dendritic cells and other immune cells sweeping out (as indicated by arrows) of the adjacent intact lung tissue and into the debris field.

FIG. 8B illustrates the dendritic cells and other immune cells moving out (as indicated by arrows) of the debris field and back into the surrounding lung tissue.

SUMMARY OF THE INVENTION

Figure 1:
FIG. 1 illustrates a tumor within a lung of a patient.

Described herein are embodiments of apparatuses, systems and methods for treating target tissue in the body. Likewise, the invention relates to the following numbered clauses:

1. A system for treating a target tissue area of a patient comprising:

an energy delivery device having at least one energy delivery body configured to be positioned near the target tissue area within the patient; and a generator in electrical communication with the at least one energy delivery body, wherein the generator includes at least one energy delivery algorithm configured to provide an electric signal of pulsed electric field energy deliverable to the at least one energy delivery body so as to induce extravasation within the target tissue area.

2. A system as in clause 1, wherein the induced extravasation is sufficient to bias molecules delivered to the target tissue area toward entry to cells of the target tissue area.

3. A system as in clause 2, wherein the molecules comprise drugs, chemotherapy drugs, immunotherapy drugs, and/or monoclonal antibodies.

4. A system as in clause 2, wherein the molecules include auxiliary materials including polymeric nanoparticles, liposomes, PEGylated liposomes, lipofectamine, cell-penetrating peptides (CPC), dimethyl sulfoxide (DMSO), cholesterol, or other materials known to interact with cell membrane fluidity and mechanics.

5. A system as in any of clauses 2-4, wherein the energy delivery device is configured to deliver the molecules to the target tissue area of the patient.

6. A system as in any of the above clauses, wherein the extravasation delivers molecules from vasculature within the target tissue area to interstitial spaces around cells within the target tissue area.

7. A system as in any of the above clauses, further comprising a controller that is configured to control delivery of the pulsed electric field energy in response to at least one component.

8. A system as in clause 7, wherein the at least one component comprises a sensor that senses a flow rate of molecules being delivered to the patient.

9. A system as in clause 7, wherein the at least one component comprises a sensor that senses pressure of a syringe pump configured to deliver molecules to the patient.

10. A system as in clause 7, wherein the at least one component comprises a timer and wherein the controller causes delivery of the pulsed electric field energy at a predetermined time after commencement of delivery of molecules to the target tissue area.

11. A system as in any of clauses 7-10, wherein the controller causes delivery of the pulsed electric field energy throughout delivery of molecules to the target tissue area.

12. A system as in any of clauses 7-11, wherein the controller causes delivery of the pulsed electric field energy throughout delivery of molecules to the target tissue area and continues 200-300% longer than the delivery of molecules.

13. A system as in any of clauses 7-11, wherein the controller causes delivery of the pulsed electric field energy throughout an additional delivery of molecules that occurs at a time period after the delivery of molecules.

14. A system as in any of the above clauses, wherein the electric signal of pulsed electric field energy deliverable to the at least one energy delivery body so as to induce extravasation within the target tissue area also causes cell death within the target tissue area.

15. A system as in clause 14, wherein the signal comprises at least two packets of biphasic pulses separated by an inter-packet delay.

16. A system as in clause 15, wherein each packet comprises 10-40 biphasic pulses.

17. A system as in clause 16, wherein each of the biphasic pulses are separated by a cycle delay of 1000 μs.

18. A system as in any of clauses 15-17, wherein each packet has an on-time of 70-100 μs.

19. A system as in any of clauses 15-18, wherein the at least two packets comprises 50-200 packets.

20. A system as in any of clauses 15-19, wherein, the inter-packet delay is in a range of 3 to 6 seconds.

21. A system as in any of clauses 15-20, wherein the electric signal has a voltage in a range of 3000V-6000V.

22. A system as in any of clauses 15-21, wherein the signal has a frequency in a range of 100-400 KHz.

23. A system as in any of clauses 1-13, wherein the generator further includes at least one additional energy delivery algorithm configured to provide an additional electric signal of pulsed electric field energy deliverable to the at least one energy delivery body so to cause cell death within the target tissue area.

24. A system as in clause 23, wherein the electric signal is comprised of a plurality of pulses having a pulse width of greater than 500 μs.

25. A system as in clause 24, wherein at least one of the plurality of pulses is separated by a delay of 10 μs-10 seconds.

26. A system as in clause 24, wherein each of the plurality of pulses is biphasic.

27. A system as in clause 26, wherein at least one of the plurality of pulses is separated by a delay of 1 μs-1 second.

28. A system as in any of clauses 23-27, wherein the additional electric signal is comprised of a plurality of pulses forming a packet, wherein each of the plurality of pulses has a duration of 0.5-200 μs, and wherein the packet has a cumulative on-time of 1-200 μs.

29. A system as in clause 28, wherein the additional electric signal comprises 40-100 packets.

30. A system as in any of the above claims, wherein the target tissue area comprises cells of a digestive system, including a liver, a pancreas, a stomach, intestines and/or colon.

31. A system as in any of clauses 1-29, wherein the target tissue area comprises cells of a respiratory system including a lung, an airway, a bronchial passageway, and/or an alveolar sac.

32. A system as in any of clauses 1-29, wherein the target tissue area comprises cells of a reproductive system including a vagina, a uterus, a cervix, a fallopian tube, an ovary, a testicle, a penis, an epididymis, a vas deferens, a urethra, a prostate gland, a seminal vesicle, and/or a bulbourethral gland.

33. A system as in any of the above clauses , wherein the target tissue area comprise at least a portion of a tumor or an abnormal growth.

34. A system as in any of the above clauses , wherein the energy delivery body is configured to function in a monopolar manner.

35. A system for treating a target tissue area of a patient comprising:

an energy delivery device configured to deliver energy to the target tissue area and configured to deliver a plurality of molecules to the target tissue area; and a generator in electrical communication with the energy delivery device, wherein the generator includes at least one energy delivery algorithm configured to provide an electric signal of pulsed electric field energy deliverable to the at least one energy delivery body that induces extravasation within the target tissue area wherein the extravasation is sufficient to bias molecules delivered to the target tissue area toward entry to cells of the target tissue area.

36. A system as in clause 35, further comprising a controller that coordinates delivery of the pulsed electric field energy and the delivery of the plurality of molecules.

37. A system as in clause 36, wherein the controller causes commencement of the delivery of the pulsed electric field energy at a predetermined time after commencement of delivery of the plurality of molecules.

38. A system as in any of clauses 36-37, wherein the controller causes simultaneous delivery of the pulsed electric field energy and delivery of molecules to the target tissue area throughout a treatment of the target tissue area.

39. A system as in clause 38, wherein the electric signal of pulsed electric field energy deliverable to the at least one energy delivery body so as to induce extravasation within the target tissue area also causes cell death within the target tissue area, and wherein treatment of the target tissue area comprises cell death within at least a portion of the target tissue area.

40. A system as in any of clauses 36-39, wherein the controller causes delivery of the pulsed electric field energy throughout delivery of molecules to the target tissue area and continues 200-300% longer than the delivery of molecules.

41. A system as in any of clauses 36-40, wherein the controller causes delivery of the pulsed electric field energy throughout an additional delivery molecules that occurs at a time period after the delivery of molecules.

42. A system as in any of the above clauses , wherein the electric signal of pulsed electric field energy deliverable to the at least one energy delivery body so as to induce extravasation within the target tissue area also causes cell death within the target tissue area.

43. A system as in clause 42, wherein the signal comprises at least two packets of biphasic pulses separated by an inter-packet delay.

44. A system as in clause 43, wherein each packet comprises 10-40 biphasic pulses.

45. A system as in any of clauses 43-44, wherein each of the biphasic pulses are separated by a cycle delay of 1000 μs.

46. A system as any of clauses 43-45, wherein each packet has an on-time of 70-100 μs.

47. A system as in any of clauses 43-46, wherein the at least two packets comprises 50-200 packets.

48. A system as in any of clauses 43-47, wherein, the inter-packet delay is in a range of 3 to 6 seconds.

49. A system as in any of clauses 43-48, wherein the electric signal has a voltage in a range of 3000V-6000V.

50. A system as in any of clauses 43-49, wherein the signal has a frequency in a range of 100-400 KHz.

51. A system as in clause 35, wherein the electric signal is comprised of a plurality of pulses having a pulse width of greater than 500 μs.

52. A system as in clause 51, wherein at least one of the plurality of pulses is separated by a delay of 10 μs-10 seconds.

53. A system as in clause 51, wherein each of the plurality of pulses is biphasic.

54. A system as in clause 53, wherein at least one of the plurality of pulses is separated by a delay of 1 μs-1 second.

55. A system as in clause 35, wherein the generator further includes at least one additional energy delivery algorithm configured to provide an additional electric signal of pulsed electric field energy deliverable to the at least one energy delivery body so as to cause cell death within the target tissue area.

56. A system as in clause 55, wherein the additional electric signal is comprised of a plurality of pulses forming a packet, wherein each of the plurality of pulses has a duration of 0.5-200 μs, and wherein the packet has a cumulative on-time of 1-200 μs.

57. A system as in any of clauses 55-56, wherein the additional electric signal comprises 40-100 packets.

58. A system as in any of clauses 35-57, wherein the target tissue area comprises cells of a digestive system, including a liver, a pancreas, a stomach, intestines and/or colon.

59. A system as in any of clauses 35-57, wherein the target tissue area comprises cells of a respiratory system including a lung, an airway, a bronchial passageway, and/or an alveolar sac.

60. A system as in any of clauses 35-57, wherein the target tissue area comprises cells of a reproductive system including a vagina, a uterus, a cervix, a fallopian tube, an ovary, a testicle, a penis, an epididymis, a vas deferens, a urethra, a prostate gland, a seminal vesicle, and/or a bulbourethral gland.

61. A system as in any of clauses 35-60, wherein the target tissue area comprise at least a portion of a tumor or an abnormal growth.

62. A system as in any of clauses 35-61, wherein the energy delivery body is configured to function in a monopolar manner.

63. A system for killing cells within a target tissue area of a patient comprising:
an energy delivery device having at least one energy delivery body configured to be positioned near the target tissue area within the patient; and
a generator in electrical communication with the at least one energy delivery body, wherein the generator includes at least one energy delivery algorithm configured to provide an electric signal of pulsed electric field energy deliverable to the at least one energy delivery body so as to induce extravasation within the target tissue area and kill cells within the target tissue area.

64. A system as in clause 63, wherein the induced extravasation is sufficient to bias molecules delivered to the target tissue area toward entry to cells of the target tissue area.

65. A system as in clause 64, wherein the molecules comprise drugs, chemotherapy drugs, immunotherapy drugs, and/or monoclonal antibodies and wherein at least some of the cells are killed by entry of the molecules.

66. A system as in any of clauses 63-65, wherein the energy delivery device includes at least one pressure sensor.

67. A system as in clause 66, wherein the at least one pressure sensor is configured to monitor effects of the extravasation and provide sensor feedback data.

68. A system as in clause 67, wherein the system includes a mechanism to provide the sensor feedback data or information based on the sensor feedback data to a user.

69. A system as in clause 68, wherein the generator includes a processor configured to modify the at least one energy delivery algorithm or switch to a different energy delivery algorithm based on the sensor feedback data so as to transmit energy which adjusts inducement of extravasation.

70. A system as in any of clauses 63-65, wherein the system includes at least one sensor.

71. A system as in clause 70, wherein the at least one sensor comprises a sensor that monitors pressure, temperature, impedance, resistance, capacitance, conductivity, pH, optical properties, coherence, echogenicity, fluorescence, electrical permittivity, light permittivity, and/or conductance.

72. A method for conditioning a target tissue area within a patient comprising:
positioning at least one electrode near the target tissue area; and
delivering pulsed electric field energy through the at least one electrode to the target tissue area, wherein the pulsed electric field energy is configured to induce extravasation causing edema within the target tissue area.

73. A method as in clause 72, further comprising delivering a plurality of molecules to the patient so that the induced extravasation increases a concentration of molecules from the plurality of molecules within the target tissue area.

74. A method as in clause 73, wherein the pulsed electric field energy is configured to treat the target tissue area and wherein delivering the plurality of molecules occurs throughout delivery of the pulsed electric field energy to treat the target tissue area.

75. A method as in clause 74, wherein treating the target tissue area comprises killing cells within the target tissue area.

76. A method as in clause 75, wherein the target tissue area comprises a tumor and wherein killing cells within the target tissue area comprises substantially destroying the tumor.

77. A method as in clause 73, wherein the pulsed electric field energy is configured to treat the target tissue area and wherein delivering the plurality of molecules occurs only during a first portion of delivery of the pulsed electric field energy to treat the target tissue area.

78. A method as in clause 77, wherein the first portion comprises 25-33% of delivery of the pulsed electric field energy to that the target tissue area.

79. A method as in clause 73, wherein the pulsed electric field energy is configured to treat the target tissue area and wherein delivering the plurality of molecules occurs only during a first portion of delivery of the pulsed electric field energy to treat the target tissue area and a last portion of delivery of the pulsed electric field energy to treat the target tissue area.

80. A method as in clause 79, wherein the first portion comprises 25% of delivery of the pulsed electric field energy to treat the target tissue area and the second portion comprises 25% of delivery of the pulsed electric field energy to treat the target tissue area.

81. A method as in clause 72, wherein the target tissue area is near vasculature of the patient and wherein the energy is configured to induce extravasation of fluid from the vasculature causing edema within the target tissue area.

82. A method as in clause 81, further comprising delivering a plurality of molecules to the vasculature and wherein the energy is configured to induce extravasation of a portion of the plurality of molecules with the fluid.

83. A method as in clause 72, wherein the target tissue area is near lymphatics of the patient and wherein energy is configured to induce extravasation of fluid from the lymphatics causing edema within the target tissue area.

84. A method as in clause 72, wherein the target tissue area comprises cells of a digestive system, including a liver, a pancreas, a stomach, intestines and/or colon.

85. A method as in clause 72, wherein the target tissue area comprises cells of a respiratory system including a lung, an airway, a bronchial passageway, and/or an alveolar sac.

86. A method as in clause 72, wherein the target tissue area comprises cells of a reproductive system including a vagina, a uterus, a cervix, a fallopian tube, an ovary, a testicle, a penis, an epididymis, a vas deferens, a urethra, a prostate gland, a seminal vesicle, and/or a bulbourethral gland.

87. A method as in clause 72, wherein the target tissue area comprises at least a portion of a tumor or an abnormal growth.

88. A method as in clause 72, further comprising delivering a second energy through the at least one electrode to the target tissue area, wherein the second energy is configured to ablate the target tissue area.

89. A method as in clause 88, wherein the second energy comprises pulsed electric field ablation energy.

90. A method as in clause 88, wherein the second energy comprises microwave ablation energy, radiofrequency ablation energy, cryoablation energy, and/or high intensity focused ultrasound (HIFU) energy.

91. A method as in clause 72, wherein the target tissue area is near vasculature of the patient and wherein the energy is configured to induce extravasation of fluid from the vasculature causing edema within the target tissue area.

92. A method for increasing a concentration of a plurality of molecules near target cells of a patient comprising:

introducing the plurality of molecules to the patient;

positioning at least one electrode within the patient; and delivering pulsed electric field energy via the at least one electrode so as to induce extravasation in a manner that increases the concentration of the plurality of molecules amongst the target cells.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Devices, systems and methods are provided for improving treatment of target tissue within a body of a patient, particularly improving treatment of tumors within a body of a patient. Tumors are typically treated by a variety of methods, including chemotherapy or the delivery of other molecules to the tumor site, either systemically or locally. The devices, systems and methods described herein provide improved outcomes, particularly as related to improvement in the uptake of molecules to the cells and ultimately increased cell death and tumor elimination.

Such devices, systems and methods involve the delivery of energy, such as pulsed electric field energy (PEF) or other suitable energy types, to induce extravasation of fluids and optionally molecules to the target tissue area. In some instances, the energy is the same as the treatment energy and in other instances the energy is different, such as a particular conditioning energy. When the energy is the same, both may be PEF energy and when the energy is different, the conditioning energy may be PEF energy and the treatment energy may be PEF energy having a different waveform or treatment parameters or the energy may be of a different type, such as microwave ablation, radiofrequency ablation, cryoablation, and/or high intensity focused ultrasound (HIFU).

In some embodiments, PEF energy is used to treat damaged, diseased, abnormal, obstructive, cancerous or undesired tissue (e.g. a tumor, a benign tumor, a malignant tumor, a cyst, or an area of diseased tissue, etc). The energy is delivered in a manner so as to be non-thermal (i.e. below a threshold for causing thermal ablation). Consequently, when extracellular matrices are present, the extracellular matrices are preserved, and the targeted tissue maintains its structural architecture including blood vessels and lymphatics. Thus, sensitive structures, such as biological lumens, blood vessels, nerves, etc, are able to be preserved which are critical to maintaining the integrity and functionality of the tissue. This provides a number of benefits. To begin, this allows for the treatment of tissues that are often considered untreatable by conventional methods. Target tissues that are near sensitive structures are typically unresectable by surgical methods due to the inability to thoroughly and effectively surgically separate the tissue from the sensitive structures. Likewise, many conventional non-surgical therapies are contraindicated due to the potential for damage to the sensitive structures by the therapy or because the therapies are deemed ineffective due to the proximity of the sensitive structures. In addition, the ability to treat tissue near sensitive structures also provides a more comprehensive treatment in that malignant margins are not left near sensitive structures. Once tissue is treated, the survival of the structural architecture also allows for the natural influx of biological elements, such as components of the immune system, or for the introduction of various agents to further the therapeutic treatment.

It may be appreciated that the energy that induces extravasation is typically referred to as conditioning energy herein throughout, however, it may be appreciated that in some instances the conditioning energy is also the treatment energy. Extravasation is typically from nearby vasculature, lymphatics, or other tissue which receives the energy. In some instances, the extravasation is edema or edema-like wherein capillaries leak fluid into the surrounding tissue. Edema occurs when an atypical volume of fluid accumulates in the tissues, either within cells (cellular edema) or within the collagen-mucopolysaccharide matrix distributed in the interstitial spaces (interstitial edema). The device, systems and methods described herein focus on swelling of the extracellular matrix or interstitial edema. Naturally occurring interstitial edema may occur as a result of aberrant changes in the pressures (hydrostatic and oncotic) acting across the microvascular walls, alterations in the molecular structures that comprise the barrier to fluid and solute flux in the endothelial wall that are manifest as changes in hydraulic conductivity and the osmotic reflection coefficient for plasma proteins, or alterations in the lymphatic outflow system. However, the devices, systems and methods described herein induce the edema or extravasation by the delivery of specialized energy. In some instances, the extravasation of fluid from the blood vessels carries molecules that are delivered intravenously into the target tissue area. In other instances, molecules are delivered regionally or locally, such as by injection, and extravasation of fluid from the blood vessels concentrates the molecules within the area of extravasation. And in still other instances, extravasation is utilized alone without the delivery of molecules, such as to condition the target tissue area for treatment.

The induced extravasation has a variety of beneficial effects for the treatment. Example improvements to the treatment therapy include, but are not limited to, conditioning the target tissue, increasing the availability of molecules, increasing the uniformity of the availability of molecules, increasing access to naturally restricted target tissues, creating larger treatment areas, and reducing potential undesired side effects, to name a few. Each of these will be described in more detail hereinbelow.

I. Overview

A. Extravasation and Treatment Methodology

The devices, systems and methods described herein are suitable for treating a variety of different types of target tissue in various anatomical locations. In some embodiments, the target tissue is abnormal tissue. Abnormal tissue can take a variety of different forms, such as damaged, diseased, obstructive, cancerous or undesired tissue. In some instances, the abnormal tissue is a tumor, such as a benign tumor or a malignant tumor, a cyst, or an area of diseased tissue. One of the most troublesome types of abnormal tissue is related to cancer. For example purposes, an embodiment related to treating a cancerous tumor in the lung anatomy is provided. However, it may be appreciated that other types of tissue may be treated and other locations of the body may be treated with the same devices, systems and methodology. For example, any tissues located sufficiently close to capillaries may be treated so as to receive the extravasation. Likewise, any tissues located sufficiently near a lumen for endoluminal access, such as near a blood vessel, an esophagus, a stomach, a pancreatic duct, a biliary duct, a small intestine, a large intestine, a colon, a rectum, a bladder, a urethra, a urinary collecting duct, a uterus, a vagina, a fallopian tube, a ureter, a renal tubule, a spinal canal, a spinal cord, an airway, a nasal cavity, a mouth, a heart chamber, a heart lumen, a kidney lumen, and an organ lumen, may be treated so as to benefit from minimally invasive access. However, it may be appreciated that tissues that are not sufficiently near a lumen may be accessed by other methods, such as percutaneously or surgically.

Figure 2:
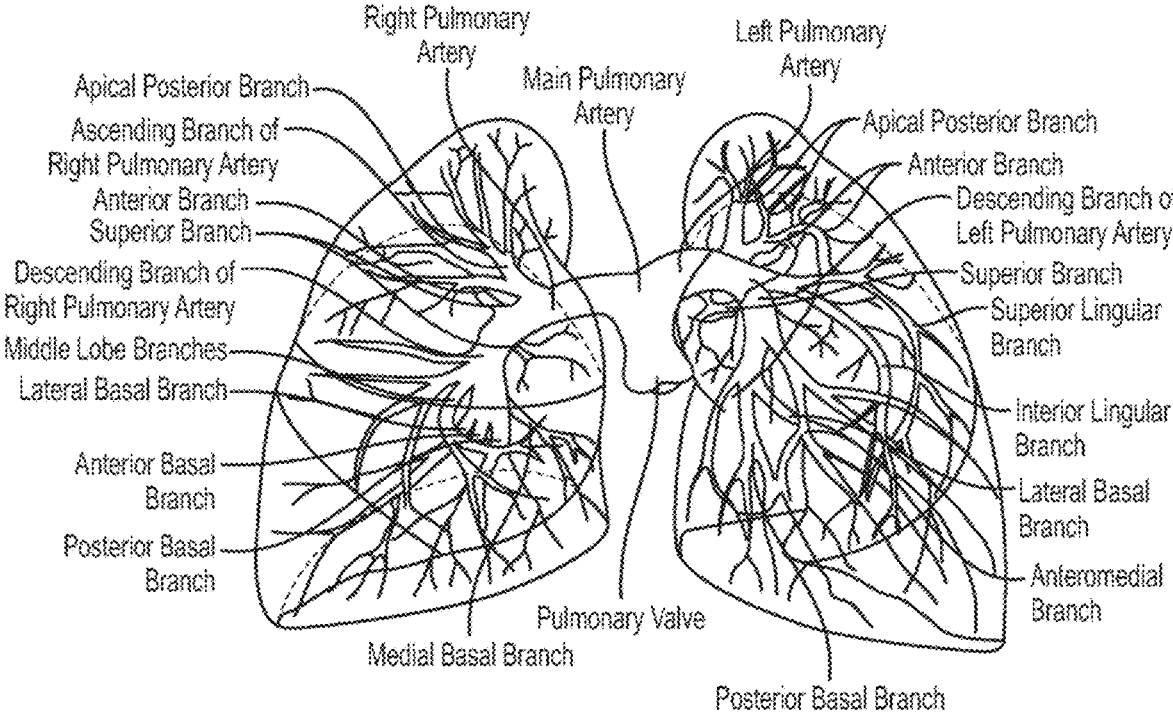
FIG. 2 schematically illustrates the pulmonary artery distribution throughout the lungs.
Figure 3:
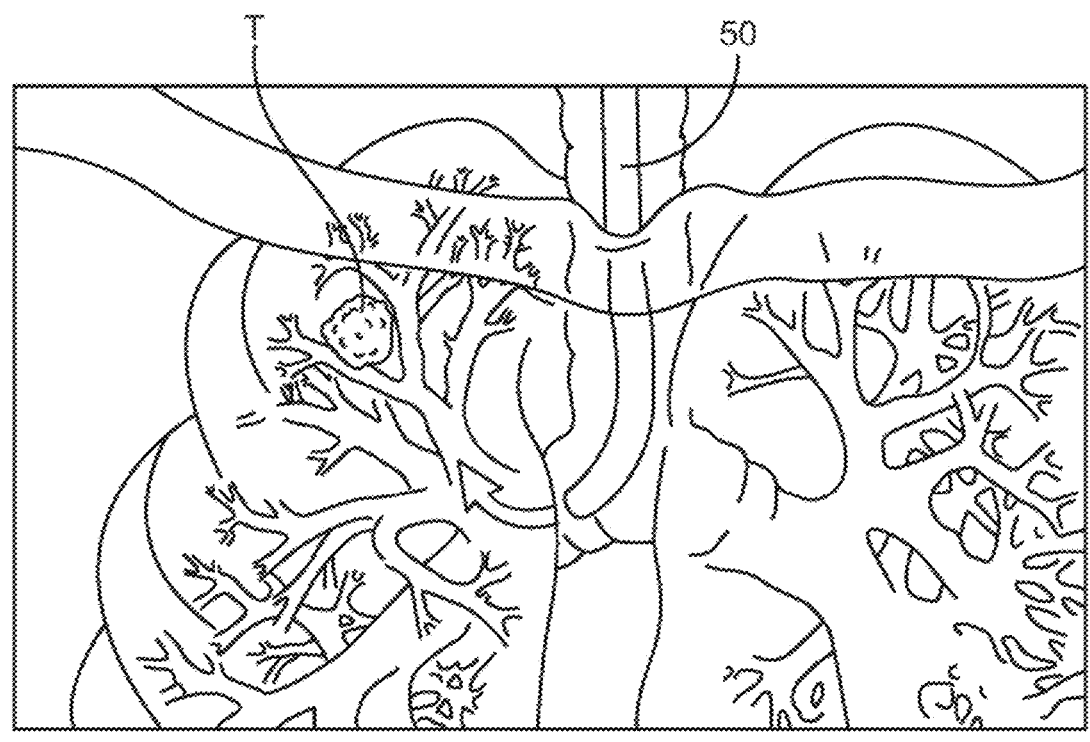
FIG. 3 illustrates an endoluminal approach to the tumor wherein a bronchoscope is advanced through the trachea and the right mainstem bronchus toward the tumor.
Figure 4:
FIG. 4 illustrates the distal end of the bronchoscope advanced through the lung passageways so as to reach the tumor.

FIG. 1 illustrates a tumor T within a lung L of a patient P. The tumor T is located within a right upper lobe of the lung L. The lung anatomy is highly vascularized, as illustrated in FIG. 2. FIG. 2 schematically illustrates the pulmonary artery distribution throughout the lungs L. Thus, many locations within the lung L are located near a blood vessel. FIG. 3 illustrates an endoluminal approach to the tumor T. Here, a bronchoscope 50 is advanced through the trachea and the right mainstem bronchus toward the tumor T. FIG. 4 illustrates the distal end of the bronchoscope 50 advanced through the lung passageways so as to reach the tumor T. A catheter or instrument or energy delivery device 102 is then advanced from the distal end of the bronchoscope 50 toward the tumor T. In this instance, the energy delivery device 102 has an elongate shaft 106 with at least one energy delivery body 108 near its distal end and a handle 110 at its proximal end. The energy delivery device 102 is connectable to a generator 104 as part of a treatment system 100, as will be described in more detail in later sections. FIG. 4 illustrates the energy delivery device 102 emerging from the bronchoscope 50, toward the wall of the lung passageway. In this embodiment, the energy delivery body 108 has the form of a needle which is able to pierce the wall of the lung passageway and the tumor T.

Figure 5A:
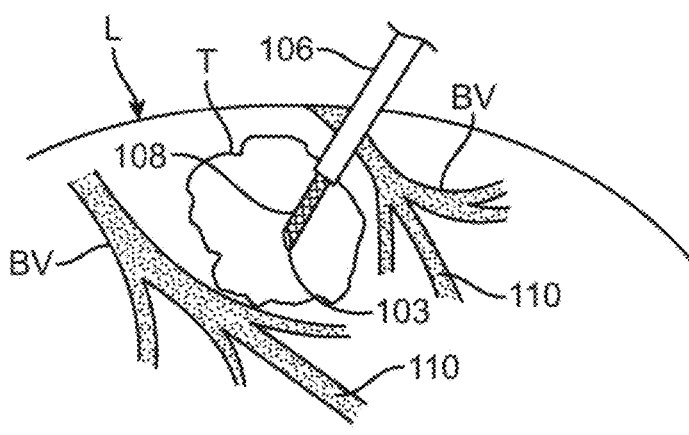
FIG. 5A illustrates a few molecules having entered the target tissue area while a significant quantity remains within the blood vessels.
Figure 5B:
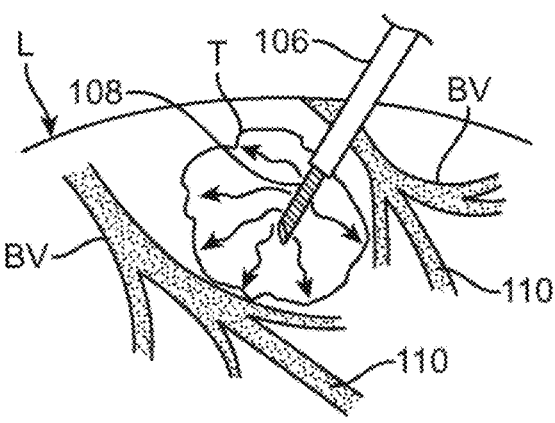
FIG. 5B illustrates conditioning energy delivered to the target tissue area from the energy delivery body as indicated by wavy lines.
Figure 5C:
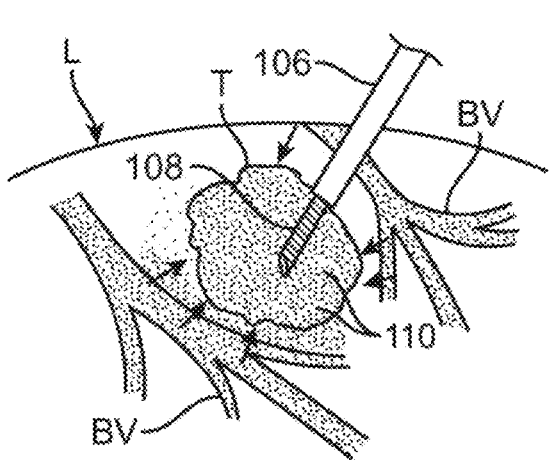
FIG. 5C illustrates extravasation and a flooding of the target tissue area with fluid and solutes, including molecules from the blood vessels.

FIGS. 5A-5C illustrate a portion of the lung L of FIG. 1 near the tumor T during stages of the extravasation procedure. In this embodiment, the energy delivery device 102 comprises an elongate shaft 106 and an energy delivery body 108 disposed near the distal end of the elongate shaft 106. As mentioned, in this embodiment, the energy delivery body 108 is comprised of a single electrode and the distal tip 103 is configured to penetrate the tumor T. It may be appreciated that in other embodiments the energy delivery body 108 has an atraumatic tip and is delivered via a separate instrument that is able to penetrate tissue. As illustrated in FIG. 5A, the energy delivery body 108 is positioned within the tumor T near blood vessels BV, such as capillaries. In this embodiment, molecules 110 are delivered to the target tissue area (e.g. tumor T) through the blood vessels BV, such as by intravenous (IV) administration. Such molecules 110 are particular to the treatment provided. In this example, the molecules 110 comprise chemotherapeutic agents to enhance the treatment effect on the tumor T. Such enhancement may increase the efficacy of therapeutic treatment or improve the ability to treat larger treatment areas, particularly with reduced possibility of thermal damage. It may be appreciated that the examples provided based on a cancerous tumor are for illustration purposes and the principles described herein may be applied to the treatment of other undesired or diseased tissues. Likewise, other drugs, agents or molecules (e.g. DNA plasmids, RNAs (e.g. messenger RNA (mRNA), small interfering RNA (siRNA), micro RNA), oligonucleotides, antisense oligonucleotides (ASO), proteins and/or materials which invoke genetic or epigenetic changes in the cellular behavior) may be delivered in the therapeutic treatment of the target tissue and is not limited to chemotherapeutic agents. Such drugs, agents and molecules will be collectively considered molecules. Example molecules will be further described in later sections. It may be appreciated that in other embodiments, the molecules 110 are delivered by the energy delivery device 102 itself or by a separate device, such as by catheter or needle injection.

FIG. 5A shows that only a few molecules 110 have entered the target tissue area but a significant quantity remains within the blood vessels BV. At least one dose of energy is then delivered to the target tissue area from the energy delivery body 108 as indicated by wavy lines 113, as illustrated in FIG. 5B. Typically, the energy comprises a specialized form of PEF energy, however it may be appreciated that other types of specialized energy may be used to cause the desired extravasation. In this embodiment, specialized PEF energy reversibly disrupts the fluid-barrier functional integrity of the endothelial cells within the blood vessels BV, such as by affecting the hydraulic conductivity and osmotic reflection coefficient for plasma proteins. This disruption causes the barrier to be less able to restrict the movement of fluid and macromolecules from the blood to the interstitium of the surrounding tissue. This causes extravasation and a flooding of the target tissue area with fluid and solutes, including molecules 110 from the blood vessels BV, as illustrated in FIG. 5C. The PEF energy typically disrupts the capillaries while causing minimal destruction of cells in the targeted area. However, it may be appreciated that such disruption may be utilized in conjunction with treatments intended to destroy cells, such as in the treatment of cancer or abnormal tissue.

This process of extravasation may occur over a period of time, such as 5 seconds, or 30 seconds to 15 minutes, however extravasation typically occurs between 30 seconds to 30 minutes. Therefore, delivery of the molecules 110 may be timed in various ways during the extravasation process so as to maximize its benefits. In some instances, it is desirable to begin delivery of the molecules 110 to the vasculature prior to delivery of the PEF energy to ensure maximum concentration and availability of the molecules 110 in the bloodstream. In some instances, it is desirable to continuously deliver molecules 110 throughout the delivery of the PEF energy. And, in other instances it is desirable to deliver molecules only at various timepoints or over various time periods during the delivery of the PEF energy. The time period of extravasation and edema generation may vary in length depending on a variety of factors including the targeted organ, parameters used, and specific objectives of the therapy. For instance, molecules 110 that are not provided at a high systemic concentration may involve maximal extravasation effects prior to and/or during the therapeutic procedure. Likewise, molecules 110 that are heavily bioavailable may involve lesser extravasation effects prior to and/or during the therapeutic procedure. It is typically desired that the blood vessels BV be at their leakiest during the period that the concentration of the molecules 110 passing through these blood vessels BV are at the highest, thus providing the greatest extravasation of molecules 110 into the targeted tissue area interstitial environment.

The induced extravasation provides a variety of advantages. Example advantages include but are not limited to creating a larger treatment area, conditioning the treatment area to be more receptive to therapeutic treatment, increasing the availability of molecules, increasing the uniformity of the availability of molecules, increasing delivery of molecules to locations that are naturally restricted, such as across the blood brain barrier, and reducing the likelihood of potential side effects of the treatment. Each of these will be described in more detail in later sections.

In this embodiment, the molecules 110 are intended to be taken up by the cells of the target treatment area. In some embodiments, the induced extravasation alone is sufficient to increase the uptake of the molecules 110 by the cells of the target tissue area. In other embodiments, uptake of the molecules 110 is further facilitated with the delivery of therapeutic energy. In some embodiments, the therapeutic energy is comprised of PEF energy having a different waveform than the pre-conditioning PEF energy. It may be appreciated that in some embodiments, the therapeutic PEF energy is delivered with the same energy delivery body 108 positioned within the target tissue area. In other embodiments, a different device is used to deliver the therapeutic energy.

It may be appreciated that in other embodiments the molecules 110 are not intended to be taken up by the cells to evoke an effect. For instance, molecules 110 comprising ligands, cytokines, tumor necrosis factor (TNF) or vascular endothelial growth factor (VEGF), etc. may be delivered to the area as part of a therapeutic treatment that does not involve uptake of these molecules 110. In such instances, the extravasation provides a variety of benefits, such as increased availability and uniformity, regardless of increased uptake.

Figure 6:
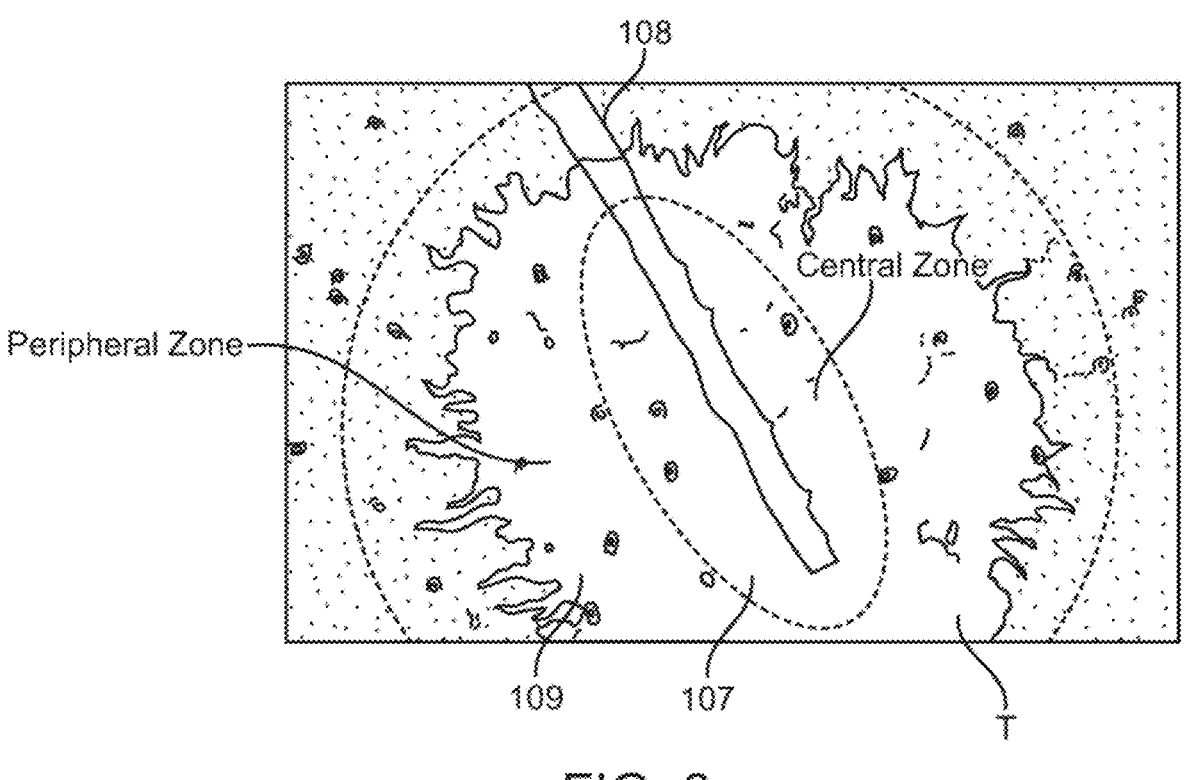
FIG. 6 illustrates an energy delivery body inserted in a tumor.

In this embodiment, the extravasation process if followed by treatment of the tumor T. FIG. 6 illustrates the energy delivery body 108 inserted in the tumor T. In this embodiment, specialized pulsed electric field (PEF) energy is delivered to target tissue areas via the energy delivery body 108. Typically, the treatment PEF energy differs from the conditioning PEF energy. However, it may be appreciated that in some instances the two energies have the same waveform or other similarities. Such therapies cause the undesired cells to be destroyed, eliminated, killed, removed, etc., while maintaining non-cellular elements, such as collagen, elastin, and matrix proteins. Therefore, the integrity and mechanical properties of the tissue, and any nearby luminal structures, are maintained while abnormal or diseased cells and tissues are sufficiently eliminated. It may be appreciated that other forms of energy or other treatment modalities may be used to treat the target tissue, such as other focal therapies including microwave ablation, radiofrequency ablation, cryoablation, and/or high intensity focused ultrasound (HIFU).

Figure 7:
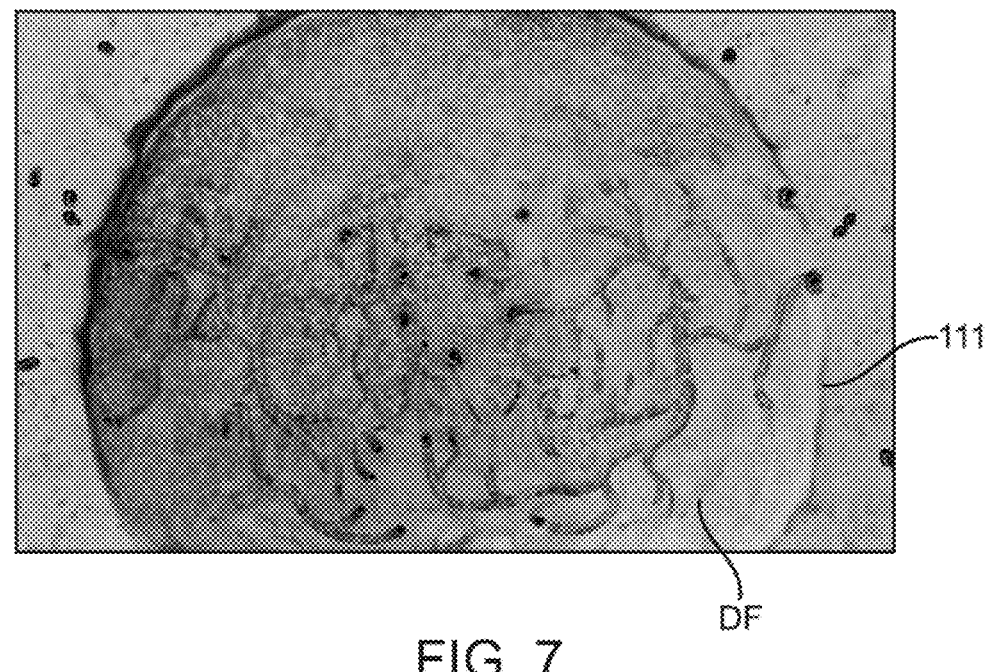
FIG. 7 illustrates that what was once a tumor is now a debris field that extends outwards to the peripheral margin.
Figure 9:
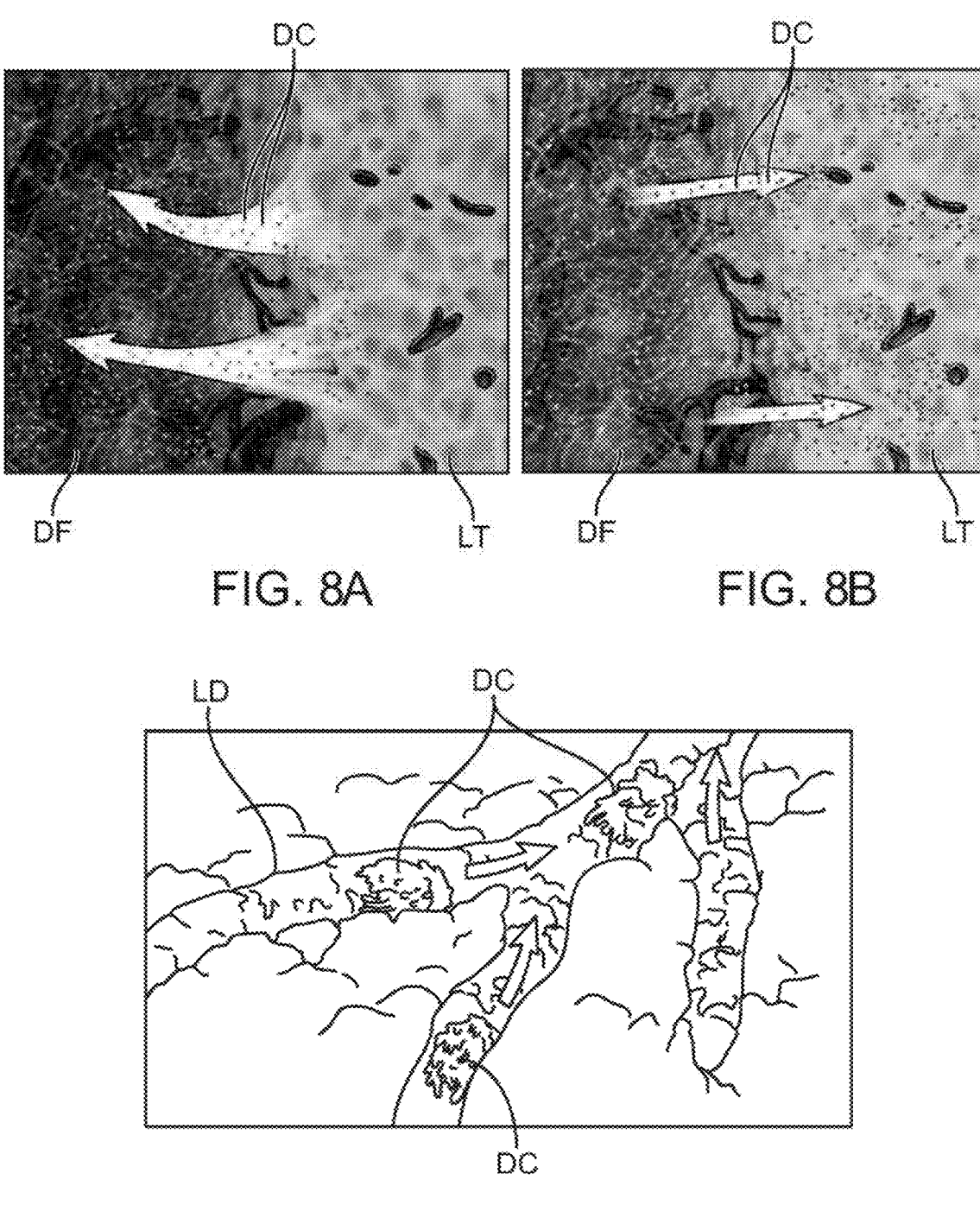
FIG. 9 illustrates dendritic cells and other immune cells entering afferent lymphatic ducts.
Figures 10, 11:
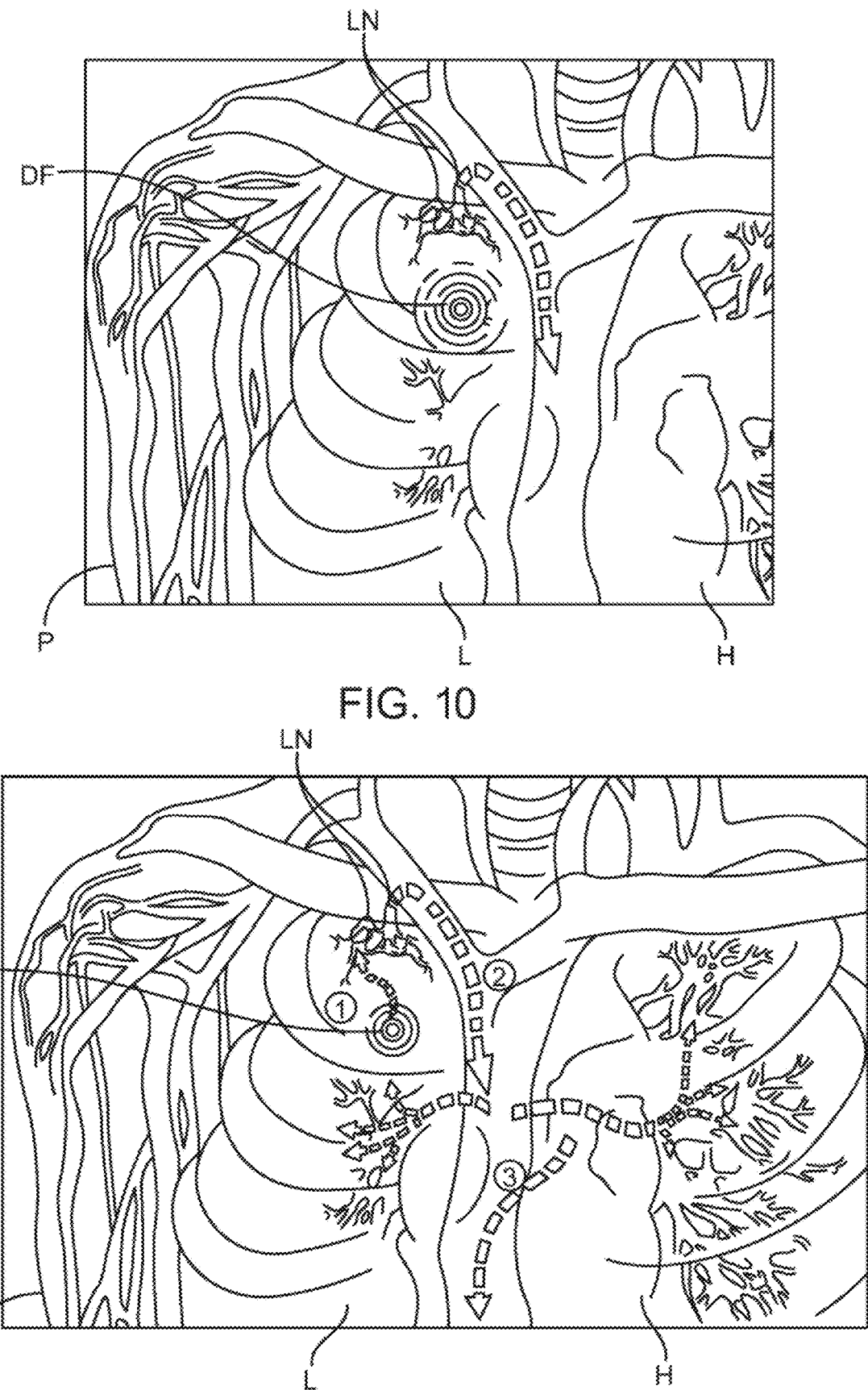
FIG. 10 illustrates the original tumor site which is now a debris field with nearby lymph nodes and activated T-cells flowing from the lymph nodes.
FIG. 11 illustrates dendritic cells and other immune cells traveling through lymphatic ducts to lymph nodes, activated T-cells traveling to the heart, and activated T-cells traveling to remote locations in the body.

In this embodiment, as illustrated in FIG. 6, the PEF energy typically creates various zones of treatment extending radially outwardly from the energy delivery body 108. As shown, a zone closest to the energy delivery body 108 (i.e. the central zone 107) endures immediate cell death, such as via necrosis. In this embodiment, a zone surrounding the central zone (i.e. the peripheral zone 109) endures delayed cell death, such as via programmed cell death. FIG. 7 illustrates that what was once a tumor T is now a debris field DF that extends outwards to the peripheral margin 111. The debris field DF is then cleared by the immune system of the patient P, as illustrated in FIGS. 8A-8B. FIG. 8A illustrates dendritic cells DC and other immune cells sweeping out (as indicated by arrows) of the adjacent intact lung tissue LT and into the debris field DF. The dendritic cells DC internalize the remaining cell fragments, antigens, and damage-associated molecular patterns (DAMPs). DAMPs are molecules released upon cellular stress or tissue injury and are regarded as endogenous danger signals because they induce potent inflammatory responses by activating the innate immune system during non-infectious inflammation. FIG. 8B illustrates the dendritic cells DC and other immune cells moving out (as indicated by arrows) of the debris field DF and back into the surrounding lung tissue LT. The dendritic cells DC and other immune cells enter afferent lymphatic ducts LD, as illustrated in FIG. 9, travel towards the nearest tumor draining lymph node and on to a network of lymph nodes LN. FIG. 10 illustrates the original tumor T site which is now a debris field DF with nearby lymph nodes LN. This causes activated T-cells to flow from the lymph nodes LN (indicated by the arrow) to the heart H which then distributes the T-cells throughout the body, including the upper right lobe of the lung L where the original tumor T resided. The T-cells then infiltrate the debris field DF via the vasculature. The residual tumor cells T are recognized by the antigens on their cell surface and the T-cells release perforin and cytotoxins to kill them. Any residual tumor cells are killed by perforin and granzymes which are released from the T-cells. In some embodiments, check-point inhibitors are provided which also support this process. Such cell death repeats the cycle through the lymph nodes LN, activating more T-cells. This may be repeated several times.

Figure 12:
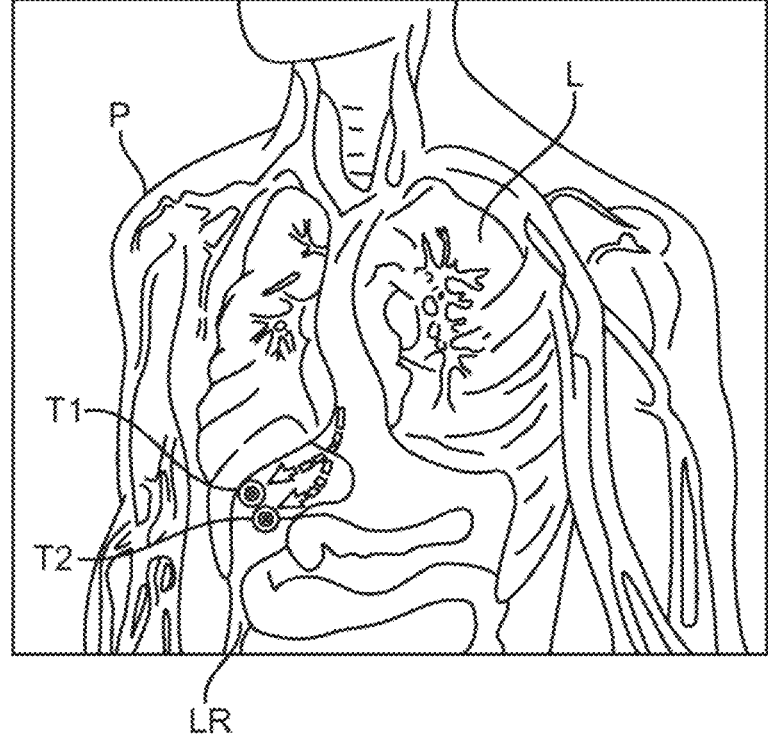
FIG. 12 illustrates the activated T-cells traveling to metastatic tumors in the liver.

In addition, the T-cells may encounter distant metastases. FIG. 11 illustrates these steps: (1) dendritic cells DC and other immune cells traveling through lymphatic ducts LD to lymph nodes LN, (2) activated T-cells traveling to the heart H, (3) activated T-cells traveling to remote locations in the body. FIG. 12 illustrates the activated T-cells of step (3) traveling to metastatic tumors T1, T2 in the liver LR. The same process then ensues in relation to the metastatic tumors T1, T2, activating more T-cells. This assists in eliminating cancerous tumors throughout the patient's body.

It may be appreciated that in some instances the lymph nodes themselves are the target tissue, such as lymph nodes which contain cancer cells, such as metastatic cancer cells. In such instances, the target lymph tissue would be treated in the same or similar manner as the tumor T described herein. This would also release activated T-cells which would travel throughout the body.

B. Extravasation Advantages

The induced extravasation may have a variety of effects that are beneficial to the therapeutic treatment provided to the target tissue area. Example improvements to the treatment therapy include, but are not limited to, conditioning the target tissue, increasing the availability of molecules, increasing the uniformity of the availability of molecules, increasing access to naturally restricted target tissues, creating larger treatment areas, and reducing potential undesired side effects, to name a few. In instances where the target tissue area is a cancerous tumor, the therapeutic treatment may include delivery of chemotherapeutic agents and/or the delivery of focal therapies, such as microwave ablation, radiofrequency ablation, cryoablation, high intensity focused ultrasound (HIFU), and pulsed electric field ablation therapies configured to destroy cells. Thus, in these instances, the induced extravasation may be considered part of a pre-conditioning or conditioning regime and would be utilized in conjunction with the therapeutic treatment (e.g. chemotherapy, focal therapy, combination of chemotherapy and focal therapy, etc.) to enhance the treatment effect. It may be appreciated that the examples provided based on a cancerous tumor are for illustration purposes and the principles described herein may be applied to the treatment of other undesired or diseased tissues. Likewise, other drugs, agents or molecules (e.g. DNA plasmids, RNAs (e.g. messenger RNA (mRNA), small interfering RNA (siRNA), micro RNA), oligonucleotides, antisense oligonucleotides (ASO), proteins and/or materials which invoke genetic or epigenetic changes in the cellular behavior) may be delivered in the therapeutic treatment of the target tissue and is not limited to chemotherapeutic agents. Such drugs, agents and molecules will be collectively considered molecules.

In some embodiments, the induced extravasation enables the generation of a larger treatment area by acting as a virtual or fluid electrode. The extravasating fluid or edema is comprised of naturally conductive material, and therefore when it gathers within the target treatment area and is in contact with the energy delivery body 108 it extends the range of the energy delivery body 108 through the conductive edema fluid. This may increase the size of an ablative lesion, such as width, depth, volume, etc. This may also increase the regional selectivity of the PEF ablation.

In some embodiments, the induced edema alters the electrical properties of the cellular microenvironment of the target tissue area. This may improve the efficiency and conduction of the therapeutic PEF energy through the target tissue area. In particular, the induced edema may reduce the electric field threshold for the cells to succumb to cell death, such as through loss of homeostasis or energy depletion. This may allow the therapeutic PEF energy protocol to use reduced intensity, reducing any potential thermal effects, easing generator demands, in addition to expanding the treatment area. Thus, in some embodiments, the induced edema normalizes the target tissue area before therapeutic treatment (such as to create a stable impedance environment). The target tissue area is typically a heterogenous environment on a microscopic scale, however the introduction of conductive fluid creates a more homogenous environment. The high conductivity fluids flow through low conductivity vessels with connective tissue, at times with no-conductivity air sacs, and other structures of widely dispersed impedances at the microscale. The more homogenous environment behaves more consistently throughout the tissue area in accordance with the new bulk-tissue conductivity. This may be beneficial when providing focal therapy alone or when providing focal therapy in combination with delivery of molecules comprising a drug or agent.

In some embodiments, the induced edema increases the local concentration of molecules 110 in the target treatment area, increasing availability of the molecules 110. When the molecules 110 are delivered via the vasculature, the extravasation of the molecules 110 from the vasculature increases the local concentration in the target treatment area. Likewise, when the molecules 110 are provided by other methods, the edema effect (e.g. increased interstitial pressure) also increases the availability of the molecules 110. It may be appreciated that due to the inability of the target tissue to readily expand its interstitial volume, relatively small increments in transcapillary fluid filtration induce large increases in interstitial fluid pressure. This creates a pressure gradient, biasing the molecules 110 toward entry to the target tissue cells. Similarly, concentration gradients which form also bias the molecules 110 toward entry to the target tissue cells.

In some instances, the induced extravasation creates an improved (e.g. more uniform) distribution of the molecules 110 throughout the target treatment area. In some instances, the induced edema provides a conduit to increase the distribution rate and final volume distribution of targeted materials that enter the interstitial space, such as via extravasation or from direct injection of the molecules 110 into the targeted region. As mentioned previously, in some embodiments, the induced edema traps the molecules in the target tissue area so that the molecules are at least temporarily resisted from diluting back into the blood or lymphatics. Ultimately, the edema is drained naturally along the lymphatics. When the edema contains molecules, the excess molecules are then drained through the lymphatics as well. In cases such as cancer, where cancer cells migrate along the lymphatics, the molecules will be brought to the same lymph nodes to which migratory cancer cells may arrive, potentially heading off metastasis.

In some embodiments, the induced extravasation increases access to naturally restricted target tissues. For example, the induced extravasation may allow delivery of materials across cellular-based tissue layers that would otherwise block passage of this material from reaching a targeted population of cells. For example, molecules 110 delivered to the vitreous humor of the eye are typically unable to reach the subretinal space, particularly the retinal pigment epithelium (RPE) and photoreceptor cells (PR). This is due to the ganglia and bipolar cells, positioned between the vitreous and the underlying RPE and PRs, which are very tightly connected. Consequently, various molecules 110, particularly large molecules, are unable to diffuse through these restrictive layers. Delivery of conditioning energy as described herein to adjacent to the surface of the retina, either deep in the intravitreal space or within a surgically produced subretinal bleb, induces extravasation of fluid from the retinal vasculature. The inner retina receives its blood supply from the retinal vasculature which is connected to the central retinal artery. At the optic disc, the central retinal artery bifurcates into several branches that provide the blood supply of the entire inner retina. The venous part of the retinal circulation is arranged in a similar way. The central retinal vein leaves the eye through the optic disc and drains blood into the cavernous sinus. The diameter of the central retinal artery before it enters the eye as well as the diameters of the branch arteries is typically below 200 mm. Hence, these vessels are functionally arterioles, and the venous vessels are functionally venules. In some embodiments, extravasation of fluid from the arterioles, capillaries, suprachoroidal space, and other regions that may carry molecules 110 accumulates in the suprachoroidal space or retinal spaces, among other regions of the eye anatomy that enable diffusion amongst the various retinal cell layers. These retinal cell layers may include those targeted in interventional PEF treatments for macromolecule uptake, including genetic transfection. Additional fluid in these environments provides a superior conduit for diffusion and dispersion of molecules injected suprachoroidally, vascularly, intravitreally, or otherwise, amongst the retinal cell layers, including the ganglia and bipolar cells, allowing increased transmission of molecules 110 from the vitreous to the subretinal space.

In another example, molecules 110 delivered to the vasculature are often unable to reach portions of the brain due to the blood-brain barrier. The blood vessels that vascularize the central nervous system (CNS) possess unique properties, termed the blood-brain barrier (BBB), which allow these vessels to tightly regulate the movement of ions, molecules, and cells between the blood and the brain. This precise control of CNS homeostasis allows for proper neuronal function and also protects the neural tissue from toxins and pathogens. The physiological barrier is coordinated by a series of physical, transport, and metabolic properties possessed by the endothelial cells (ECs) that form the walls of the blood vessels, and these properties are regulated by interactions with different vascular, immune, and neural cells. However, delivery of conditioning energy as described herein disrupts the blood-brain barrier so as to allow the molecules 110 to pass through to deeper cells in the brain. Thus, the PEF energy may be utilized to disrupt the BBB, disrupt the BBB with the inclusion of molecules 110 to act as an adjuvant (e.g. calcium, chemotherapy, immunostimulants, charge-modulating materials, etc), or disrupt the BBB with molecules 110 to transfect into cells (e.g. chemotherapy or genetic material including RNAs, DNA, plasmids, oligos, etc), to name a few.

It may be appreciated that in other embodiments, the molecules 110 are delivered via the cerebral spinal fluid rather than via the vasculature. Such access may be achieved by spinal tap. This may permit direct access of the molecules 110 into the regions of the central nervous system, such as the ventricles of the brain. The PEFs may then be used to encourage regional edema to promote the distribution and diffusion of the molecules 110 into regions beyond the ventricles. It may be appreciated that, in a variety of clinical applications, edema may be used to promote migration and distribution of molecules 110 regardless of how the molecules 110 were initially delivered. Thus, the induced extravasation of fluid may be used as a secondary delivery mechanism that assists the primary delivery.

In yet another example, molecules 110 delivered to blood vessels throughout the body are often unable to reach the innermost layers of the lumen walls, such as for treating the blood vessels themselves. In some instances, passage of molecules 110 through the endothelial lining of blood vessels is challenging. Such passage is typically desired to deliver drugs and other agents to the smooth muscle layer and beyond. This may be desired in the prevention of restenosis when treating occluded blood vessels. In some embodiments, conditioning energy is transmitted to the lumen wall causing extravasation of the molecules 110 from the lumen through one or more layers of the lumen wall.

In some embodiments, the induced extravasation reduces the likelihood of secondary effects from the treatment devices, such as potential arcing and/or thermal effects. This occurs due to the thermal sink effects of fluid in a target environment, as well as the nature of most edematous fluids described herein being conductive. Thus, in regions where the target electrode may not have ideal electrical contact at the tissue-electrode interface (either weak contact, or only partial contact with the remainder contacting air or other low-conductivity tissues), the fluid may serve as an electrical interface to deliver the PEF energy from the electrode into the surrounding tissue.

For example, in some instances, an electrode placed in aerated lung parenchymal tissue will have sporadic electrical contact with tissue, resulting in very high electrical currents at the sites of tissue contact. This results in inefficient PEF energy distribution into the tissue which may cause thermal effects, such as carbonization and caramelization of tissue, and may cause electrical arcing from the electrode to the tissue. However, after delivering therapeutic or subtherapeutic PEF energy into the tissue, the edematous fluid will locally fill the aerated alveolar regions, particularly those in closest proximity to the electrode. This fluid will then distribute the PEF energy more evenly throughout the tissue. This allows the delivery of stronger PEF treatment protocol waveforms without the potential of causing arcing, burning, or other adverse collateral effects.

In addition to spreading the energy more efficiently, edematous filling within a region to improve electrical continuity at the tissue-electrode interface can also encourage a farther dispersion of the energy before experiencing much voltage drop, essentially expanding the effective surface area of the electrode via a "virtual electrode" effect. This reduces the intensity of the energy needed to deliver the same treatment effects. This in turn eases generator demands.

It may be appreciated that in some embodiments, the conditioning energy increases the cellular resistance of the target tissue area to eventual cell death. This may be desired when the treatment involves procedures such as gene transfection rather than ablation. In such instances, uptake of genetic material by the cells is desired rather than elimination or destruction of the cells. In such instances, the target treatment area receives the conditioning energy causing extravasation of fluid into the area. It is known that cells experiencing sub-lethal stresses will generate reparative and preventative responses to stress, in essence developing resistance to subsequent stresses of a similar or different nature, strengthening their resilience. For example, in some embodiments, the conditioning energy causes heat shock proteins (HSPs) to be released. HSPs are a family of proteins that are produced by cells in response to exposure to stressful conditions, such as conditioning energy as described herein. Although HSPs were initially described in relation to heat shock, HSPs are now known to also be expressed during other stresses including exposure to cold, UV light and during wound healing or tissue remodeling. Many members of this group perform chaperone functions by stabilizing new proteins to ensure correct folding or by helping to refold proteins that were damaged by the cell stress. This increase in expression is transcriptionally regulated. The dramatic upregulation of the heat shock proteins is a key part of the heat shock response and is induced primarily by heat shock factor (HSF).

In some embodiments, pre-warming of the tissue or cells (prior to the delivery of the molecules 110) may start expression of heat-shock proteins, which play a role in cell injury, repair and survival. In such embodiments, a warm solution, such as warm saline, may be injected to the treatment site wherein the molecules 110 are delivered after a wait period along with the delivery of energy. The wait period may be minutes, hours or days after the delivery of the warming solution. In some embodiments, the wait period is 5-30 min, 1-2 hours or 1-2 days.

In other embodiments, the tissue or cells are warmed with the use of the energy delivery body 108. In such embodiments, the energy is delivered at a controlled rate to maintain local temperature within a specific range, such as between 40-50C for a treatment of less than 10 minutes. It may be appreciated that in some embodiments, heat-shock proteins are triggered around approximately 41C. Thus, sub-lethal pulsed electric field delivery may be used to encourage upregulation of heat-shock proteins and other damage-repair preparation prior to the stronger treatment pulsed electric fields. This encourages cell resilience to injury from the pulsed electric fields and improves the ability to transfer molecules to a meaningful number of cells without undesired excessive cell death. Thus, in one embodiment, conditioning energy is delivered to the target treatment area which elevates temperatures in at least a portion of the treatment area, such as to 45 degrees Celsius. This induces extravasation of fluid to the area. A drug, gene, or other type of molecule is delivered via intratumoral injection and benefits from the advantages of extravasation as describe herein. Therapy, such as therapeutic PEF energy is then delivered to the target treatment area. Since the cells of the treatment area were previously conditioned to resist cell death, a greater number of cells survive the treatment protocol. This is beneficial for gene therapy or other types of therapy which rely on cell survival.

II. Delivery System Embodiments

Figure 13:
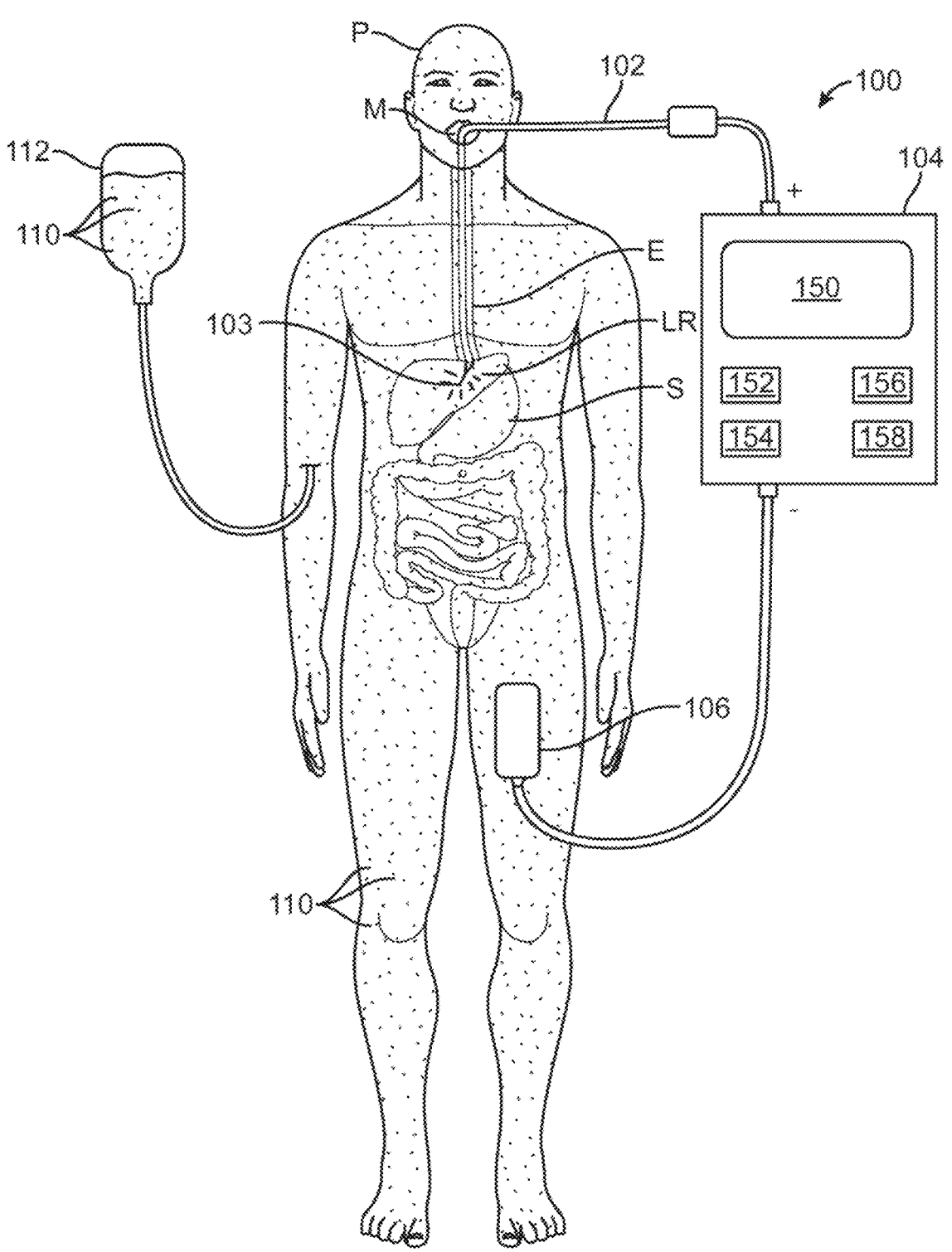
FIG. 13 illustrates an embodiment of an energy delivery system for delivering energy to a target tissue area.

As mentioned, the devices, systems and methods described herein generate extravasation and interstitial edema by delivering pulsed electric field (PEF) or other mixed-lethal or sub-lethal energy to the target tissue area which induces alterations, such as in the endothelial walls of capillaries within and optionally near the target tissue area. FIG. 13 illustrates an embodiment of an energy delivery system 100 for delivering such PEF energy to the target tissue area. In this embodiment, the system 100 comprises a specialized energy delivery device 102, a return electrode 106, and a waveform generator 104. In this embodiment, the target tissue area is located within a liver LR of a patient P, however it may be appreciated that such devices, systems and methods may be used to treat target tissue areas throughout the body. In this embodiment, the energy delivery device 102 comprises a flexible elongate shaft having a distal end capable of being advanced endoluminally to the target tissue within the liver LR. As shown, the distal end of the delivery device 102 is advanced through the mouth M, down the esophagus E, into the stomach S wherein it passes through the stomach wall into the liver LR. In some embodiments, the distal end has a distal tip 103 configured to penetrate the stomach wall and/or the liver LR. In other embodiments, a passageway is formed through the stomach wall with the use of a separate instrument which is then removed so that an energy delivery device 102 having an atraumatic tip is able to be passed through the passageway. It may be appreciated that in other embodiments the energy delivery device 102 is percutaneous.

Examples of systems which may provide this type of therapeutic treatment are provided in commonly assigned patent application PCT/US2020/028844, entitled "DEVICES, SYSTEMS AND METHODS FOR THE TREATMENT OF ABNORMAL TISSUE", incorporated herein by reference for all purposes. Other example systems include the pulmonary tissue modification systems (e.g., energy delivery catheter systems) described in commonly assigned patent applications including international patent application number PCT/US2017/039527 titled "GENERATOR AND A CATHETER WITH AN ELECTRODE AND A METHOD FOR TREATING A LUNG PASSAGEWAY," which claims priority to U.S. provisional application No. 62/355,164 and 62/489,753, international patent application number PCT/US2018/067501 titled "METHODS, APPARATUSES, AND SYSTEMS FOR THE TREATMENT OF DISORDERS" which claims priority to U.S. Provisional Application No. 62/610,430, and international patent application number PCT/US2018/067504 titled "OPTIMIZATION OF ENERGY DELIVERY FOR VARIOUS APPLICATIONS" which claims priority to Provisional Patent Application No. 62/610,430 filed Dec. 26, 2017 and U.S. Provisional Patent Application No. 62/693,622 filed Jul. 3, 2018, all of which are incorporated herein by reference for all purposes.

As mentioned, the conditioning PEF energy and optionally the therapeutic energy is delivered to the target tissue through the distal end of the delivery device 102. The proximal end of the delivery device 102 is electrically connected with the waveform generator 104. In some embodiments, the generator 104 is also connected with an external cardiac monitor to allow coordinated delivery of energy with the cardiac signal sensed from the patient P.

The energy is provided by the generator 104 and delivered to the tissue through an energy delivery body 108 placed on, in, or near the targeted tissue area. Electric pulses are then delivered through the energy delivery body 108 in the vicinity of the target tissue. These electric pulses are provided by at least one energy delivery algorithm 152. In such embodiments, the algorithm 152 specifies parameters of the signal such as energy amplitude (e.g. voltage) and duration of applied energy, which is comprised of the number of pulses, the pulse widths and the delay between pulses, to name a few. In some embodiments, one or more of the energy delivery bodies are small and tend to dissipate large amount of energy around the electrode. Therefore, an optimal delivery of energy is desired. Typically, large DC-link capacitance with half transistor bridges is the recommended generator structure to deliver efficient delivery pulses in such instances. Pulse voltages delivered by power amplifiers (limited bandwidth) or exponential decay generators are not as desirable for this application.

In some embodiments, biphasic pulses may be used. In such embodiments, additional parameters may include switch time between polarities in biphasic pulses and dead time between biphasic cycles. A feedback loop based on sensor information and an auto-shutoff specification, and/or the like, may be included. Biphasic waveforms are convenient to reduce muscle stimulation in patients. This is particularly important in the application where slight movement of the energy delivery body can easily result a non-effective procedure. Biphasic waveforms involve rapid change of phases/polarities of the signal to minimize nerve activation during transition between polarity. Multiple fast switching elements (e.g. MOSFET, IGBT Transistors) are desired and are employed and configured in, for example, H-bridge structure or full bridge.

Referring back to FIG. 13, in this embodiment the generator 104 includes a user interface 150, one or more energy delivery algorithms 152, a processor 154, a controller 155, a data storage/retrieval unit 156 (such as a memory and/or database), and an energy-storage sub-system 158 which generates and stores the energy to be delivered. In some embodiments, one or more capacitors are used for energy storage/delivery, however any other suitable energy storage element may be used. In addition, one or more communication ports may be included.

In some embodiments, the generator 104 includes three sub-systems: 1) a high-energy storage system, 2) a high-voltage, medium-frequency switching amplifier, and 3) the system controller, firmware, and user interface. The generator takes in alternating current (AC) mains to power multiple direct current (DC) power supplies. The generator's controller can cause the DC power supplies to charge a high-energy capacitor storage bank before energy delivery is initiated. In some embodiments, at the initiation of energy delivery, the generator's controller, high-energy storage banks and a bi-phasic pulse amplifier can operate simultaneously to create a high-voltage, medium frequency output.

It will be appreciated that a multitude of generator electrical architectures may be employed to execute the energy delivery algorithms. In particular, in some embodiments, advanced switching systems are used which are capable of directing the pulsed electric field circuit to the energy delivering electrodes separately from the same energy storage and high voltage delivery system. Further, generators employed in advanced energy delivery algorithms employing rapidly varying pulse parameters (e.g., voltage, frequency, etc.) or multiple energy delivery electrodes may utilize modular energy storage and/or high voltage systems, facilitating highly customizable waveform and geographical pulse delivery paradigms. It should further be appreciated that the electrical architecture described herein above is for example only, and systems delivering pulsed electric fields may or may not include additional switching amplifier components.

The user interface 150 can include a touch screen and/or more traditional buttons to allow for the operator to enter patient data, select a treatment algorithm (e.g., energy delivery algorithm 152), initiate energy delivery, view records stored on the storage/retrieval unit 156, and/or otherwise communicate with the generator 104.

In some embodiments, the user interface 150 is configured to receive operator-defined inputs. The operator-defined inputs can include a duration of energy delivery, one or more other timing aspects of the energy delivery pulse, power, and/or mode of operation, or a combination thereof. Example modes of operation can include (but are not limited to): system initiation and self-test, operator input, algorithm selection, pre-treatment system status and feedback, energy delivery, post energy delivery display or feedback, treatment data review and/or download, software update, or any combination or subcombination thereof.

In some embodiments, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data, such as related to the treatments delivered, and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. Each of these algorithms 152 may be executed by the processor 154.

In some embodiments, the energy delivery device 102 includes one or more sensors that can be used to determine temperature, impedance, resistance, capacitance, conductivity, pH, optical properties (coherence, echogenicity, fluorescence), electrical or light permittivity, and/or conductance, to name a few. In some embodiments, one or more of the electrodes act as the one or more sensors. In other embodiments, the one or more sensors are separate from the electrodes.

Sensor data can be used to plan the procedure, monitor the procedure and/or provide direct feedback via the processor 154, which can then alter the energy-delivery algorithm 152. For example, impedance measurements can be used to determine not only the initial dose to be applied but can also be used to determine the need for further energy delivery, or not.

It may be appreciated that in some embodiments the system 100 includes an automated delivery algorithm that dynamically responds and adjusts and/or terminates delivery in response to inputs such as temperature, impedance at various voltages or AC frequencies, time duration or other timing aspects of the energy delivery pulse, power and/or system status.

In this embodiment, molecules 110 are delivered systemically, intravenously with the use of an IV bag 112. This typically disperses the molecules throughout the body of the patient P, including to the target tissue within the liver LR. It may be appreciated that in other embodiments, the molecules 110 are delivered regionally. In such embodiments, the molecules 110 may be delivered to the vasculature, upstream of the arterial system that leads to the targeted organ or tissue area. The molecules 110 then travel through the downstream arterial circulation into the targeted region. If a bolus injection of the molecules 110 is provided, a sudden rush of molecules 110 will enter into the targeted tissue. However, if the molecules 110 are delivered over time, such as with the use of an infusion pump, a steady, sustained level of molecules 110 may be achieved in the targeted tissue. It may be appreciated that in other embodiments, the molecules 110 are delivered by direct injection to the targeted tissue. In such embodiments, the injection device is inserted in or near the targeted tissue, such as within the parenchymal tissue of the targeted organ region, and a solution containing the molecules 110 is injected. It may be appreciated that any combination of systemic, regional and local delivery may alternatively be used.

In some embodiments, the conditioning PEF energy is delivered prior to, during and/or after delivery of the molecules 110, but before the therapeutic treatment, so as to improve the later uptake or effect of the molecules 100 on the cells within the target tissue area. Thus, it may be understood that the molecules 110 can be delivered before, during and/or after delivery of the conditioning PEF. In other embodiments, the conditioning PEF energy and the treatment PEF energy are one in the same and in such instances the molecules 110 may be delivered before, during and/or after the delivery of the treatment PEF energy. Various methodologies of timing and procedure will be described in greater detail in later sections.

III. Molecules and Enhancements

As mentioned previously, in some embodiments the devices, systems and methods are provided for delivering molecules 110, particularly small molecules and/or macromolecules, to cells within the body, such as to target cells. In some embodiments, the cells directly therapeutically benefit from the functionality of the molecules. Such therapeutic benefit may be in the treatment of a variety of disorders.

In some embodiments, the disorder comprises a coagulation disorder, such as hemophilia (e.g., hemophilia A or hemophilia B), von Willebrand's disease, factor XI deficiency, a fibrinogen disorder, or a vitamin K deficiency. The coagulation disorder may be characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism. In some embodiments, the coagulation disorder is characterized by a mutation in FGA, FGB, FGG, F2, F5, F7, F10, F11, F13A, F13B, LMAN1, MCFD2, GGCX, or VKORC1.

In some embodiments, the disorder comprises a neurological disorder, e.g., a neurodegenerative disease. In some embodiments, the neurodegenerative disease comprises Alzheimer's disease, Parkinson's disease, or multiple sclerosis. In some embodiments, the neurodegenerative disease comprises an autoimmune disease of the central nervous system (CNS), such as multiple sclerosis, encephalomyelitis, a paraneoplastic syndrome, autoimmune inner ear disease, or opsoclonus myoclonus syndrome. The neurological disorder may be a cerebral infarction, spinal cord injury, central nervous system disorder, a neuropsychiatric disorder, or a channelopathy (e.g., epilepsy or migraine). The neurological disorder may be an anxiety disorder, a mood disorder, a childhood disorder, a cognitive disorder, schizophrenia, a substance related disorders, or an eating disorder. In some embodiments, the neurological disorder is a symptom of a cerebral infarction, stroke, traumatic brain injury, or spinal cord injury.

In some embodiments, the disorder comprises a lysosomal storage disorder, such as Tay-Sachs disease, Gaucher disease, Fabry disease, Pompe disease, Niemann-Pick disease, or mucopolysaccharidosis (MPS).

In some embodiments, the disorder comprises a cardiovascular disorder, such as a degenerative heart disease, a coronary artery disease, an ischemia, angina pectoris, an acute coronary syndrome, a peripheral vascular disease, a peripheral arterial disease, a cerebrovascular disease, or atherosclerosis. The cardiovascular disorder may be a degenerative heart disease selected from the group consisting of an ischemic cardiomyopathy, a conduction disease, and a congenital defect.

In some embodiments, the disorder comprises an immune disorder, e.g., an autoimmune disorder. The autoimmune disorder may be type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

In some embodiments, the disorder comprises a liver disease, such as hepatitis, Alagille syndrome, biliary atresia, liver cancer, cirrhosis, a cystic disease, *Caroli*'s syndrome, congenital hepatic fibrosis, fatty liver, galactosemia, primary sclerosing cholangitis, tyrosinemia, glycogen storage disease, Wilson's disease, or an endocrine deficiency. The liver disease may be a liver cancer such as a hepatocellular hyperplasia, a hepatocellular adenoma, a focal nodular hyperplasia, or a hepatocellular carcinoma.

In some embodiments, the disorder comprises a cancer, such as a blood cancer (e.g., acute lymphoblastic leukemia, acute myeloblastic leukemia, chromic myelogenous leukemia, Hodgkin's disease, multiple myeloma, and non-Hodgkin's lymphoma) or a solid tissue cancer (e.g., liver cancer, kidney cancer, a breast cancer, a gastric cancer, an esophageal cancer, a stomach cancer, an intestinal cancer, a colorectal cancer, a bladder cancer, a head and neck cancer, a skin cancer, or a brain cancer).

In some embodiments, the disorder comprises a recessively inherited disorder. In some embodiments, the disorder is a Mendelian-inherited disorder.

In some embodiments, the disorder comprises an ocular disorder that is a retinal dystrophy (e.g., a Mendelian-heritable retinal dystrophy). The retinal dystrophy may be comprised of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and choriorretinopathy, retinitis pigmentosa, CSNB 2, Usher syndrome, or Wagner syndrome.

In some embodiments, the molecules 110 delivered by the devices, systems and methods described herein include synthetic DNA vectors, such as those described in Publication No. WO2019178500 filed on Mar. 15, 2019, entitled "Synthetic DNA Vectors and Methods of Use," incorporated in its entirety herein for all purposes. Such synthetic DNA vectors include non-viral DNA vectors, such as those that provide long-term transduction of quiescent cells (e.g., post-mitotic cells) in a manner similar to AAV vectors. In some embodiments, such non-viral DNA vectors are development by an in vitro (e.g., cell-free) system to synthetically produce circular AAV-like DNA vectors (e.g., DNA vectors containing a terminal repeat sequence, such as a DD element) by isothermal rolling-circle amplification and ligation-mediated circularization (as opposed to bacterial expression and site-specific recombination, for example). Such development allows for improved scalability and manufacturing efficiency in production of circular AAV-like DNA vectors. Moreover, the vectors produced by these methods are designed to overcome many of the problems associated with plasmid-DNA vectors, e.g., problems discussed in Lu et al., Mol. Ther. 2017, 25(5): 1187-98, which is incorporated herein by reference in its entirety. For example, by eliminating or reducing the presence of CpG islands and/or bacterial plasmid DNA sequences such as RNAPII arrest sites, transcriptional silencing can be reduced or eliminated, resulting in increased persistence of the heterologous gene. Further, by eliminating the presence of immunogenic components (e.g., bacterial endotoxin, DNA, or RNA, or bacterial signatures, such as CpG motifs), the risk of stimulating the host immune system is reduced. Such benefits are especially advantageous in the treatment of certain disorders, such as retinal dystrophies (e.g., Mendelian-heritable retinal dystrophies).

Thus, such vectors include synthetic DNA vectors that: (i) are substantially devoid of bacterial plasmid DNA sequences (e.g., RNAPII arrest sites, origins of replication, and/or resistance genes) and other bacterial signatures (e.g., immunogenic CpG motifs); and/or (ii) can be synthesized and amplified entirely in a test tube (e.g., replication in bacteria is unnecessary, e.g., bacterial origins of replication and bacterial resistance genes are unnecessary). In some embodiments, the vectors contain a double-D (DD) element characteristic of AAV vectors. This allows a target cell to be transduced with a DNA vector having a heterologous gene that behaves like AAV viral DNA (e.g., having low transcriptional silencing and enhanced persistence), without needing the virus itself.

In some embodiments, the molecules 110 include nucleic acid-based molecules, such as small interfering RNA (siRNA), short hairpin RNA (shRNA), oligonucleotides, antisense oligonucleotide (ASO), microRNA (miRNA), decoy DNA, ribozyme, morpholino and plasmid.

RNA interference using small inhibitory RNA (siRNA) can be used to downregulate mRNA levels by cellular nucleases that become activated when a sequence homology between the siRNA and a respective mRNA molecule is detected. Therefore, in some embodiments, siRNA is used to silence genes involved in the pathogenesis of various diseases associated with a known genetic background. In some embodiments, the molecules 110 comprise Patisiran, an siRNA-based drug FDA approved for the treatment of polyneuropathy in people with hereditary transthyretin-mediated amyloidosis. In order for the siRNA to function, the siRNA must be inside the target cell of interest. This means the siRNA must be transported to the tissue in the body where the target cells reside and then it must cross through the cell's membrane. These requirements are generally referred to as "delivery" of the siRNA to the desired location. Delivery has proved difficult in conventional delivery methods because siRNAs are negatively charged molecules that do not naturally cross through a cell's outer membrane. The devices, systems and methods described herein overcome these delivery difficulties, delivering the siRNA into the target cells.

In some embodiments, the molecules 110 include microRNAs (miRNAs). miRNAs are a class of small noncoding RNAs of ~22 nt in length which are involved in the regulation of gene expression at the posttranscriptional level by degrading their target mRNAs and/or inhibiting their translation.

In some embodiments, the molecules 110 include antisense oligonucleotides (ASO). ASOs are synthetic DNA oligomers that hybridize to a target RNA in a sequence-specific manner. In some embodiments, ASOs are delivered to inhibit gene expression, modulate splicing of a precursor messenger RNA, or inactivate microRNAs. In order to stabilize ASO against nucleolytic degradation, chemically modified nucleotides such as phosphorothioates, 2'-O-methyl RNA, or locked nucleic acids may be used because they confer nuclease resistance. In some embodiments, ASOs are delivered with optimization of enhanced delivery, specificity, affinity, and nuclease resistance with reduced toxicity.

Example ASOs include (1) Fomivirsen, such as for treatment of CMV retinitis in AIDS patients, (2) Mipomersen, such as for treatment of familial hypercholesterolemia, (3) defibrotide, such as for treatment of veno-occlusive disease in the liver, (4) Eteplirsen, such as for the treatment of Duchenne muscular dystrophy, (5) pegaptanib, such as for the treatment of neovascular age-related macular degeneration, and (6) Nusinersen, such as for the management of spinal muscular atrophy.

In some embodiments, the molecules 110 include oligomer molecules, such as phosphorodiamidate Morpholino oligomer (PMO), also known as Morpholino, a type of oligomer molecule used to modify gene expression knocking down gene function. Usually 25 bases in length, Morpholinos bind to complementary sequences of RNA or single-stranded DNA by standard nucleic acid base-pairing. A Morpholino oligo specifically binds to its selected DNA or RNA target site to block access of cell components to that site. This property can be exploited to block translation, block splicing, block microRNAs (miRNAs) or their targets, and block ribozyme activity. Its molecular structure contains DNA bases attached to a backbone of methylenemorpholine rings linked through phosphorodiamidate groups. Because the uncharged backbone of the Morpholino oligo is not recognized by enzymes, it is completely stable to nucleases. In some embodiments, the Morpholino-based drug, eteplirsen, is delivered which may be used in the treatment of some mutations causing Duchenne muscular dystrophy (DMD). In other embodiments, the Morpholino-based drug, golodirsen, is delivered for DMD treatment.

In some embodiments, the molecules 110 include ribozymes (ribonucleic acid enzymes) which are naturally occurring RNA molecules that catalyze specific biochemical reactions, including RNA splicing in gene expression, similar to the action of protein enzymes. In some embodiments, the molecules 110 comprise synthetic ribozymes, such as designed to inhibit the production of proteins through the specific cleavage of the disease-causing mRNA. Another application of ribozyme therapy includes the inhibition of RNA-based viruses such as HIV, hepatitis C virus, SARS coronavirus (SARS-COV), Adenovirus and influenza A and B virus.

In some embodiments the molecules 110 comprise a ribonucleoprotein (RNP). RNP is a complex formed between RNA and RNA-binding proteins. For instance, purified Cas9 Protein can be combined with guide RNA to form an RNP complex to be delivered to cells for rapid and highly efficient genome editing. RNPs remain in the cell for a short time and the dose is minimal, leading to lower toxicity and reduced editing at off-target sites compared to other methods. RNP complex are also DNA-free lacking therefore insertional mutagenesis risks.

In some embodiments, the molecules 110 delivered by the devices, systems and methods described herein include Clustered Regularly Interspaced Short Palindromic Repeats Repetitive (CRISPR) DNA sequences, called CRISPR. These DNA sequences were originally observed in bacteria with "spacer" DNA sequences in between the repeats that exactly match viral sequences. It was subsequently discovered that bacteria transcribe these DNA elements to RNA upon viral infection. The RNA guides a nuclease (a protein that cleaves DNA) to the viral DNA to cut it, providing protection against the virus. The nucleases are named "Cas," for "CRISPR-associated."

In 2012, researchers demonstrated that RNAs could be constructed to guide a Cas nuclease (Cas9 was the first used) to any DNA sequence. The so-called guide RNA can also be made so that it will be specific to only that one sequence, improving the chances that the DNA will be cut at that site and nowhere else in the genome. Further testing revealed that the system works quite well in all types of cells, including human cells.

With CRISPR/Cas, a targeted gene is able to be disrupted, or, if a DNA template is added to the mix, a new sequence is able to be inserted at a precise spot desired. The method has been used to develop animal models with specific genomic changes. And for human diseases with a known mutation, such as cystic fibrosis, it is theoretically possible to insert DNA that corrects the mutation. However, it has been difficult to deliver the CRISPR/Cas material to mature cells in large numbers using conventional methods such as viral vectors. However, the devices, systems and methods described herein overcome these difficulties allowing molecules 110 comprising CRISPR/Cas material to be delivered to cells.

In some embodiment the molecules 110 comprise recombinant protein. With the use of recombinant DNA technology, such therapeutic proteins have been developed to treat a wide variety of disease, including cancers, autoimmunity/inflammation, exposure to infectious agents, and genetic disorders.

In some embodiments the molecules 110 comprise a proteolysis targeting chimera (PROTAC). PROTAC is a small molecule capable of removing specific unwanted proteins. PROTACs are comprised of two covalently linked protein-binding molecules: one capable of engaging an E3 ubiquitin ligase, and another that binds to a target protein meant for degradation. Recruitment of the E3 ligase to the target protein results in ubiquitination and subsequent degradation of the target protein by the proteasome. PROTACs may be employed in the degradation of different types of target proteins related to various diseases, including cancer, viral infection, immune disorders, and neurodegenerative diseases.

PROTAC has various advantages in cancer therapy such as overcoming drug resistance and degrade traditionally "undruggable" protein target. At present, only 20-25% of the known protein targets can be targeted by using conventional drug discovery technologies. The proteins that lack catalytic activity and/or have catalytic independent functions are still regarded as "undruggable" targets. Moreover, large amount of oncoproteins, such as transcriptional factors, chromatin modulators and small GTPases, are hard to be directly targeted pharmaceutically. PROTAC is designed to target protein of interest (usually oncoprotein) for degradation by hijacking the endogenous E3 ligase and ubiquitin proteasome system.

In some embodiments, the molecules 110 are comprised of antineoplastic drugs such as chemotherapy. Chemotherapy drugs include agents such as alkylating compounds (e.g. Cisplatin), nitrosoureas (e.g. Carmustine), anti-metabolites (e.g. Fluorouracile), alkaloids (e.g. Taxol), antibiotics (e.g. Doxorubicin), Corticosteroid hormones and sex hormones (e.g. Dexamethasone and Tamoxifen), topoisomerase inhibitors (e.g. Etoposide) and retinoids (e.g. all trans retinoid acid ATRA).

In some embodiments, the molecules 110 comprise immunotherapy drugs such as checkpoint inhibitors. Immune checkpoint inhibitors work by blocking checkpoint proteins from binding with their partner proteins. This prevents the "off" signal from being sent, allowing the T cells to kill cancer cells.

In some embodiments, the molecules 110 are immunotherapy drugs such as T-cell transfer therapy. This therapy enhances the ability of the body's T cells to fight cancer. Immune cells are extracted from the tumor and those identified as the most active against the tumor are further modified to better attack the cancer cells. Once enough cells have been grown, the cells are injected back into the body to fight the disease.

In some embodiments, the molecules 110 comprise immunotherapy drugs such as cancer vaccines. These vaccines are administered to trigger an immune response against certain cancers. This boosts the immune system's response against the cancer cells. Example cancer vaccines include the following vaccines approved by the U.S. Food and Drug Administration that prevent cancer: 1) HPV vaccine, this vaccine protects against the human papillomavirus (HPV) which predispose to cervical cancers. 2) Hepatitis B vaccine to protect against the hepatitis B virus (HBV) which causes liver cancer.

In some embodiments, the molecules 110 comprise immune system modulators. Types of immune-modulating agents include: Cytokines (e.g. interferons, interleukins) and Immunomodulatory drugs (e.g. Thalidomide).

In some embodiments, the molecules 110 comprise monoclonal antibodies. Monoclonal antibodies (mAbs) are lab-created immune system proteins (antibodies) that are designed to bind to specific proteins on cancer cells. These proteins bind to the cancer cells, allowing them to be recognized and destroyed by the immune system. Many monoclonal antibodies are used to treat cancer (e.g. Avastin, Herceptin). Some monoclonal antibodies are also immunotherapy because they help turn the immune system against cancer (e.g. anti PD-1, anti-PDL-1, anti-CTLA-4, anti-CD20, anti-CD19).

The ability to deliver the molecules 110 to the tissue or cells may be altered with the use of a variety of enhancements. For example, in some embodiments, ancillary/auxiliary materials are added to the body, such as added to a solution carrying the molecules, wherein the auxiliary materials render the cells more susceptible to small molecule or macromolecule uptake. Example auxiliary materials include polymeric nanoparticles, liposomes, PEGylated liposomes, lipofectamine, cell-penetrating peptides (CPC), dimethyl sulfoxide (DMSO), cholesterol, or other materials known to interact with cell membrane fluidity and mechanics. In some embodiments, the auxiliary material is injected, and the injection pressure is chosen or adjusted to enhance uptake of the molecules 110 by the cells.

In other embodiments, the tissue or cells are warmed or cooled to alter their ability to successfully receive the molecules 110. For example, in some embodiments, the cells are warmed or cooled, such as by warming or cooling a solution carrying the molecules 110, to invoke better transfer efficiency or improved likelihood of cell survival following energy delivery. In some embodiments, warming of the cells may increase membrane fluidity and therefore increase acceptance of the molecules 110. In other embodiments, cooling of the cells may increase rigidity and potential formation of "cracks" which increase acceptance of the molecules 110.

As mentioned previously, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters, one or more measured tissue parameters, and/or a combination thereof. In some embodiments, the parameter includes temperature so that temperature is able to be maintained within a specific range by controlling the cadence of energy delivery. This may be useful for enhancing cell uptake, immune response, overall safety, etc.

It may be appreciated that enhancements may be applied before, during or after delivery of the molecules 110 and/or before, during or after delivery of the treatment energy. In some embodiments, auxiliary material is administered to the patient at a desired interval during a multi-function waveform, such as between a short high pulse and a long low pulse of an asymmetric waveform. This may assist in driving or pushing the auxiliary material into the cells.

It may be appreciated that in some embodiments, isotonic or hypertonic saline solution is delivered to the treatment site to adjust local tonicity.

IV. Example Waveforms

Figure 14A:
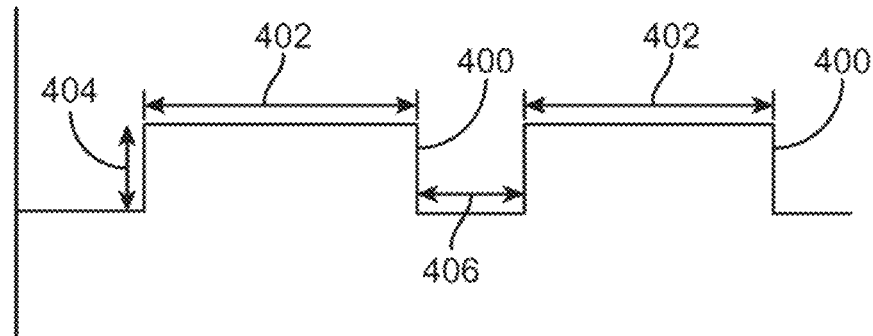
FIGS. 14A-14B illustrate an example waveforms of pulsed electric field energy provided by an energy delivery algorithm of the generator used for inducing extravasation.
Figure 14B:
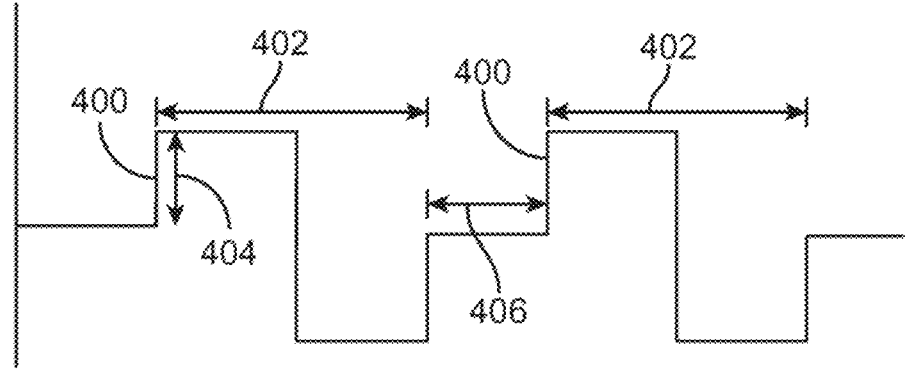

In some embodiments, the conditioning PEF energy has a waveform comprising monophasic, long-duration (>500 μs) pulses. FIG. 14A illustrates an example waveform of such PEF energy provided by an energy delivery algorithm 152 of the generator 104 used for inducing extravasation. In this embodiment, the waveform is comprised of a series of pulses 400, each having a pulse width 402 and amplitude (determined by the set voltage 404), wherein each pulse 400 is separated by a delay 406. In this embodiment, the pulse width is considered long duration and is greater than 500 microseconds. In this embodiment, the delay 406 between pulses 400 is in a range of 10 μs to 10s, including 10 μs-100 μs, 1 ms-100 ms, 100 ms-500 ms, 500 ms-1 second, 1-5 seconds, 5-10 seconds, 1 ms, 500 ms, 1 second, 2 seconds, 5 seconds. In FIG. 14A, two pulses 400 are illustrated, however conditioning may be achieved with one, two, three, four, five, six, seven, eight, nine, ten, or more than ten pulses. In some embodiments, this PEF energy is not designed to induce uptake of the molecules 110 by cells within the target tissue area and therefore may utilize a range of pulse parameters (e.g. voltage, frequency, inter-pulse delays, etc.). However, it may be appreciated that in some embodiments, the treatment energy itself may be similar to that of FIG. 14A. In some embodiments, the waveform is biphasic, such as illustrated in FIG. 14B. Here, each pulse 400 is biphasic and has a pulse width 402 separated by a delay 406. In this embodiment, the pulse width 402 is again considered long duration and is greater than 500 microseconds. In this embodiment, the delay 406 between pulses 400 is in a range of 1 μs to 1 second, such as 1 μs to 10 μs, 10 μs, 1 μs to 100 μs, 100 μs, 1 μs to 250 μs, 250 μs, 1 μs to 500 μs, 500 μs, 1 ms, 2 ms, 5 ms or 1-5 ms, to name a few. It may be appreciated that in some embodiments, the pulses 400 reverse polarity such that some pulses 400 have a positive amplitude and some pulses 400 have a negative amplitude; such reverses in polarity may be symmetric or asymmetric. It may also be appreciated that in some embodiments, the pulses 400 are grouped by polarity. It may be appreciated that any suitable number of pulses may be present in each group, and each group may have the same or differing numbers of pulses. For example, six positive pulses may be followed by two negative pulses or four positive pulses may be followed by one negative pulse. Thus, various combinations can be made. Such groupings may be symmetrical or non-symmetrical. Further, although FIG. 13 illustrates monopolar delivery utilizing the specialized energy delivery device 102 and return electrode 106, the PEF energy may be delivered with bipolar electrodes, such as bipolar electrode arrays.

Figure 15A:
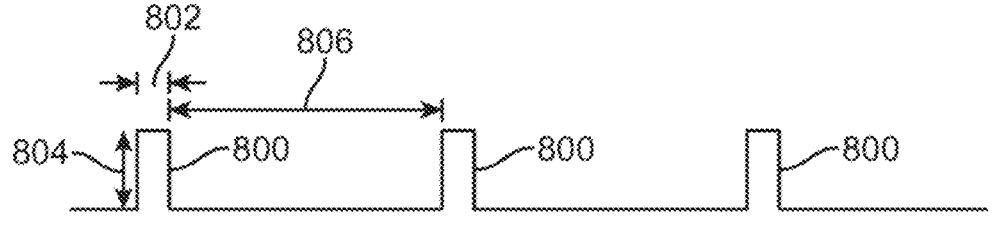
FIGS. 15A-15B, 16A-16B illustrate example waveforms provided by an energy delivery algorithm of the generator used for providing therapeutic treatment.
Figure 15B:
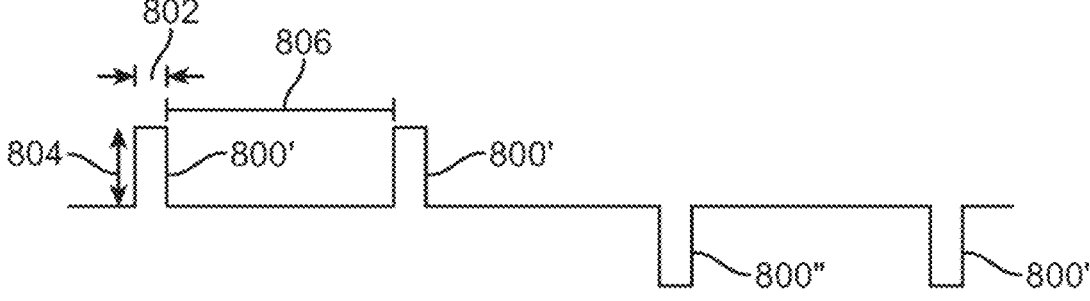

FIG. 15A illustrates an example waveform provided by an energy delivery algorithm 152 of the generator 104 used for providing a therapeutic treatment. Rather than long-duration (>500 μs) pulses configured for inducing extravasation, these waveforms have short duration pulses 0.5-200 μs which may be combined in multiple manners to result in a cumulative on-time of 1-200 μs comprising a packet; after which multiple packets may be delivered as configured for a treatment, such as for ablating targeted regions of tissue. It may be appreciated that such PEF energy may also induce extravasation. In this embodiment, the waveform is comprised of a series of low voltage, low frequency pulses 800, each having a pulse width 802 and amplitude (determined by the set voltage 804), wherein each pulse 800 is separated by a delay 806. Such a waveform may be suited for transfer of genetic material to cells. In this embodiment, three pulses 800 are illustrated, however transfer may be achieved with one, two, three, four, five, six, seven, eight, nine, ten, or more than ten pulses. It may be appreciated that in some embodiments, the pulses 800 reverse polarity such that some pulses 800 have a positive amplitude and some pulses 800 have a negative amplitude. It may also be appreciated that in some embodiments, the pulses 800 are grouped by polarity. For example, FIG. 15B illustrates an example waveform provided by an energy delivery algorithm 152 wherein two pulses 800' have a positive polarity followed by two pulses 800" that have a negative polarity. It may be appreciated that any suitable number of pulses may be present in each group, and each group may have the same or differing numbers of pulses. For example, six positive pulses may be followed by two negative pulses or four positive pulses may be followed by one negative pulse. Thus, various combinations can be made. Such groupings may be symmetrical or non-symmetrical. Likewise, the pulses 800 may have differing characteristics, such as differing amplitudes (determined by the set voltage 804) and pulse widths 802.

In some embodiments, the therapeutic energy is delivered in a monopolar fashion and the amplitude of each pulse or the set voltage 804 is 1-500V, 1-250V, 1-100V, 10-100V, 10-70V, 10-50V, 10-40V, 10-30V, 10-20V, 10V, 20V, 30V, 40V, 50V, 60V, 70V, 80V 90V, 100V, to name a few. The voltages used and considered may be the tops of square-waveforms, may be the peaks in sinusoidal or sawtooth waveforms, or may be the RMS voltage of sinusoidal or sawtooth waveforms.

It may be appreciated that the set voltage 804 may vary depending on whether the energy is delivered in a monopolar or bipolar fashion. In bipolar delivery, a lower voltage may be used due to the smaller, more directed electric field. The bipolar voltage selected for use in therapy is dependent on the separation distance of the electrodes, whereas the monopolar electrode configurations that use one or more distant dispersive pad electrodes may be delivered with less consideration for exact placement of the catheter electrode and dispersive electrode placed on the body. In monopolar electrode embodiments, the dispersive electrode may be comprised of a pad or any other recipient electrode. Typically, it functions as a dispersive electrode due to its size (large enough to prevent invoking effects locally where it is placed) and/or due to its placement (far enough away to avoid local effects and to not risk electrical arcing). However, in some embodiments, the dispersive electrode is small and may have some effects at its placement site, however such effects may be benign collateral effects. For example, the delivered molecules 110 may not be present near the dispersive electrode so as to avoid delivery or any delivery in the area is inconsequential. In monopolar electrode embodiments, larger voltages are typically used due to the dispersive behavior of the delivered energy through the body to reach the dispersive electrode, on the order of 10 cm to 100 cm effective separation distance. However, it may be appreciated that separation distance may be as low as 2 cm-5 cm in some embodiments, with typically 5 cm being the minimum for a reasonably sized dispersive electrode. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance.

In some embodiments, the pulse width 802 is 1 ms, 2 ms, 5 ms, 10 ms, 20 ms, 30 ms, 40 ms, 50 ms, 60 ms, 70 ms, 80 ms, 90 ms, 100 ms, 1 ms-100 ms, 2 ms-100 ms, 1-2 ms, to name a few. In some embodiments, the delay between pulses is 0.01-5 seconds, 0.01-0.1 seconds, 0.01-0.5 seconds, 0.01-1 second, 0.5 seconds, 0.5-1 second, 1 second, 1-1.5 seconds, 1-2 seconds, 0.5 to 2 seconds, 2 seconds, 1-3 seconds, to name a few. In some embodiments, the number of pulses is 1 pulse, 2 pulses, 3 pulses, 4 pulses, 5 pulses, 6 pulses, 7 pulses, 8 pulses, 9 pulses, 10 pulses, more than 10 pulses to name a few.

Figure 16A:
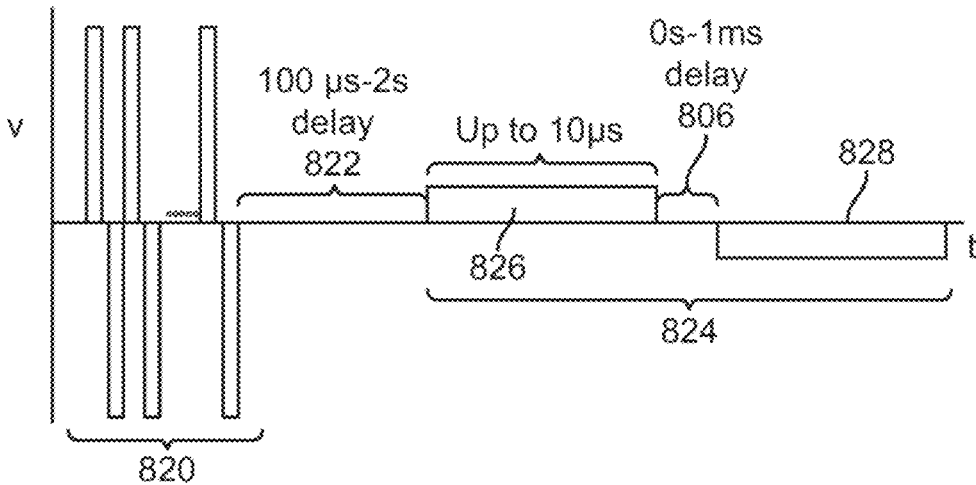

In some embodiments, the therapeutic energy comprises a series of high voltage, high frequency pulses are followed by a series of low voltage, low frequency pulses wherein the combination has particular effects on the target cells. For example, as illustrated in FIG. 16A, a first set of pulses 820 is delivered wherein the first set of pulses 820 comprises a plurality of high voltage, high frequency pulses, optionally in packets. Examples of such high voltage, high frequency pulses are provided in U.S. Pat. No. 10,702,337, entitled "Methods, apparatuses, and systems for the treatment of pulmonary disorders" and PCT/US2020/028844, entitled "DEVICES, SYSTEMS AND METHODS FOR THE TREATMENT OF ABNORMAL TISSUE", incorporated herein by reference, to name a few. Such pulses may prepare the cells for uptake of molecules 110 by the cells. In some embodiments, the first set of pulses 820 is followed by a delay 822 (such as 100 microseconds to 2 seconds) which is then followed by a second set of pulses 824. In this embodiment, the second set of pulses 824 is comprised a plurality of low voltage, low frequency pulses. FIG. 16A illustrates a first pulse 826 of the second set of pulses 824 lasting up to 10 microseconds followed by a delay 806 (e.g. up to 1 ms) and then a second pulse 828. In this embodiment, the second pulse 828 has opposite polarity to the first pulse 826, therefore the delay 806 may be considered a switch time delay 807. It may be appreciated that in some embodiments, there is no delay 806/807 between the pulses 826, 828. In some instances, the first set of pulses 820 prepares the cells for the uptake of molecules 110, such as putting them into a state that is more receptive to receiving the molecules or a transfer process. Thus, the first set of pulses 820 starts the process. The second set of pulses 824 then assist in getting the molecules into the cells, such as the driving or pushing the molecules into the cells. Optionally, these sets of pulses 820, 824 may be repeated in a pattern.

Figure 16B:
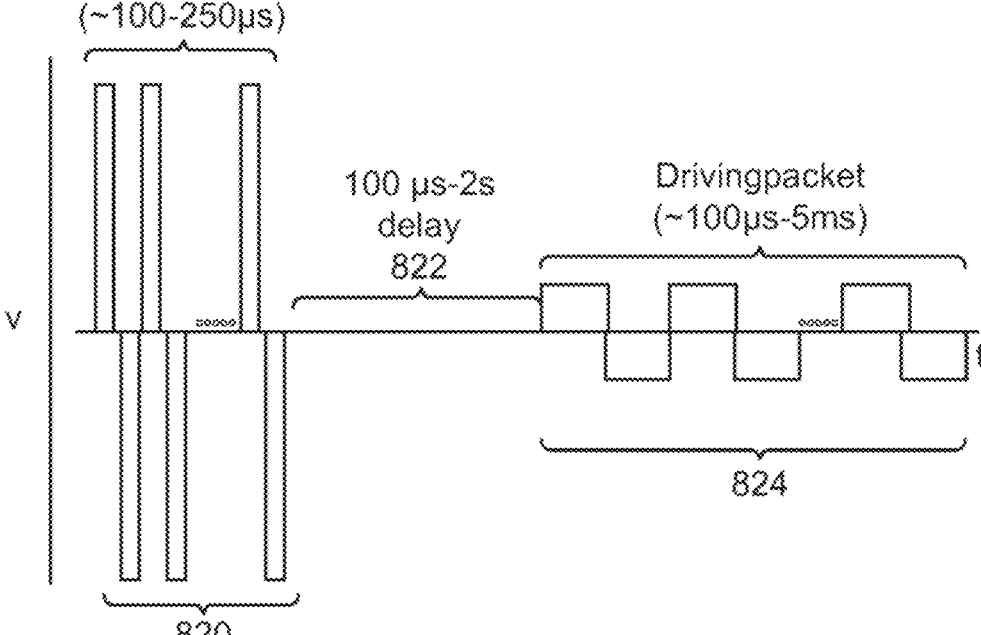

FIG. 16B illustrates another example of waveform having varied segments. Here, the first set of pulses 820 is delivered wherein the first set of pulses 820 comprises a plurality of high voltage, high frequency pulses, optionally in packets. Again, examples of such high voltage, high frequency pulses are provided in U.S. Pat. No. 10,702,337, entitled "Methods, apparatuses, and systems for the treatment of pulmonary disorders" and PCT/US2020/028844, entitled "DEVICES, SYSTEMS AND METHODS FOR THE TREATMENT OF ABNORMAL TISSUE", incorporated herein by reference, to name a few. In some embodiments, the first set of pulses 820 is followed by a delay 822 (such as 100 microseconds to 2 seconds) which is then followed by a second set of pulses 824. In this embodiment, the second set of pulses 824 is comprised a plurality of low voltage, low frequency pulses. In this embodiment, the second set of pulses 824 is comprised of a series of biphasic pulses having no switch time delay, wherein the second set of pulses 824 lasts approximately 100 microseconds to 5 milliseconds. Again, in some instances, the first set of pulses 820 prepares the cells for the uptake of molecules 110, such as putting them into a state that is more receptive to receiving the molecules or a transfer process. Thus, the first set of pulses 820 starts the process. The second set of pulses 824 then assist in getting the molecules into the cells, such as the driving or pushing the molecules into the cells. Optionally, these sets of pulses 820, 824 may be repeated in a pattern.

Thus, in some embodiments, the system 100 includes an algorithm 152 to generate a waveform having a first set of pulses 400 designed to induce extravasation followed (optionally after a significant delay to allow time for the edema effect to maximally occur) by a second set of pulses 800 designed to provide therapeutic treatment. When the therapeutic treatment involves uptake of molecules 110 by the target cells, the second set of pulses 800 are typically configured to increase uptake of the molecules 110. In some embodiments, the therapeutic treatment involves intracellular transfection of genetic material into cells. Considerations for this objective include the need to move the large, oftentimes electrically charged, genetic materials to the surface of the cells at the cell membranes, as well as pushing them across the cell membrane, with potential enhancement from temporary disruptions to the cell membrane integrity. This can be attained by longer duration, monophasic or biphasic sequences of PEFs. In this way the plasmid that is residing within the interstitial fluid is introduced into the cells to enact its downstream objectives.

Optionally, the second set of pulses 800 may comprise a plurality of different types of pulses, such as a set of pulses 820 comprising a plurality of high voltage, high frequency pulses followed by a set of pulses 826 comprising a plurality of low voltage, low frequency pulses. In such instances, the overall waveform may comprise three sets of pulses: 1) an extravasation inducing set of pulses 400, 2) a set of high voltage, high frequency pulses 820, and 3) a set of low voltage, low frequency pulses 826. Such combinations of pulses may maximize the uptake of molecules 110 by the target cells.

It may be appreciated that the delivery of PEF energy for extravasation and therapeutic treatment may be supplemented with the inclusion of secondary methods of fostering either of these objectives. For instance, when the molecules 110 comprise plasmid, an agent such as lipofectamine could be mixed with the plasmid to encourage cellular uptake. This may enhance transfection in regions that were first bathed in the plasmid+lipofectamine mixture via extravasation induction from the capillary disrupting PEF energy.

Typically, the conditioning PEF energy disrupts the capillaries with minimal or no destruction of target tissue cells. The extent and ratio of killed cells to disrupted capillaries would vary with different target organs and conditions being treated. For instance, in hepatic applications, collateral cell death to the hepatocytes is generally more tolerable due to the regenerative nature of this organ. Thus, liver-targeted PEF first (or second) wave protocols may have increased intensity (voltage, lower frequency, longer duration, more of them) in comparison to more sensitive organs to generate regional edema to a larger volume. Conversely, targets such as the brain or heart may not afford much tolerance for collateral cell death, and thus treatments in these target organs may involve using weaker protocols that cause edema in smaller volumes so as to prevent excessive cell death in these sensitive organs.

In some embodiments, conditioning PEF energy is utilized in conjunction with a therapeutic treatment comprising ablation and/or an immunological response, either alone or in combination with molecules comprising drugs or agents, such as chemotherapeutic agents. In such instances, extravasation is induced by the conditioning PEF, such as to normalize the target tissue area before therapeutic treatment (such as to create a stable impedance environment) and/or expands the target treatment area by creating a virtual or fluid electrode. This may be particularly the case when utilizing conditioning PEF energy in combination with therapy without the inclusion of molecules for uptake by the cells. Such therapeutic treatments may include microwave ablation, radiofrequency ablation, cryoablation, high intensity focused ultrasound (HIFU), and/or pulsed electric field therapies. Examples of systems and waveforms which provide this type of ablative pulsed electric field therapeutic treatment include the pulmonary tissue modification systems (e.g., energy delivery catheter systems) described in commonly assigned patent applications including international patent application number PCT/US2017/039527 titled "GENERATOR AND A CATHETER WITH AN ELECTRODE AND A METHOD FOR TREATING A LUNG PASSAGEWAY," which claims priority to U.S. provisional application Nos. 62/355,164 and 62/489,753, international patent application number PCT/US2018/067501 titled "METHODS, APPARATUSES, AND SYSTEMS FOR THE TREATMENT OF DISORDERS" which claims priority to U.S. Provisional Application No. 62/610,430, and international patent application number PCT/US2018/067504 titled "OPTIMIZATION OF ENERGY DELIVERY FOR VARIOUS APPLICATIONS" which claims priority to Provisional Patent Application No. 62/610,430 filed Dec. 26, 2017 and U.S. Provisional Patent Application No. 62/693,622 filed Jul. 3, 2018, all of which are incorporated herein by reference for all purposes.

In some embodiments, the focal therapy is used in combination with molecules 110, such as drugs or agents. Thus, the conditioning extravasation and edema may improve the focal therapy, the uptake of the molecules 110 by the cells, or both. When the molecules 110 are delivered in combination with focal therapy, the molecules 110 may act as a neoadjuvant therapy. Neoadjuvant therapies may be used in cancer treatment and are delivered before the primary treatment, to help reduce the size of a tumor or kill cancer cells that have spread.

In some embodiments, the molecules 110 comprise chemotherapeutic drugs. Chemotherapy is typically a systemic therapy that is introduced into the bloodstream, so it is, in principle, able to address cancer at any anatomic location in the body. Traditional chemotherapeutic agents are cytotoxic by means of interfering with cell division but cancer cells vary widely in their susceptibility to these agents. To a large extent, chemotherapy can be thought of as a way to damage or stress cells, which may then lead to cell death if apoptosis is initiated. Many of the side effects of chemotherapy can be traced to damage to normal cells that divide rapidly and are thus sensitive to anti-mitotic drugs, particularly cells in the bone marrow, digestive tract and hair follicles. Chemotherapy may also be administered locally to the tumor tissue.

In some embodiments, conditioning PEF energy is used to induce extravasation and edema which increases the concentration of chemotherapy in the target tissue area. In addition, the target tissue is treated with therapeutic PEF energy. Such treatment disrupts cellular homeostasis, which can initiate a programmed cell death-like effect which leads to permanent cell death or priming of the cells for more effective damage by the chemotherapy. Such priming provides a synergy between the therapeutic PEF treatment and the chemotherapy leading to outcomes that exceed either treatment alone. Thus, such combinatory treatment can lead to more effective treatment and greatly improved responses.

Figure 17:
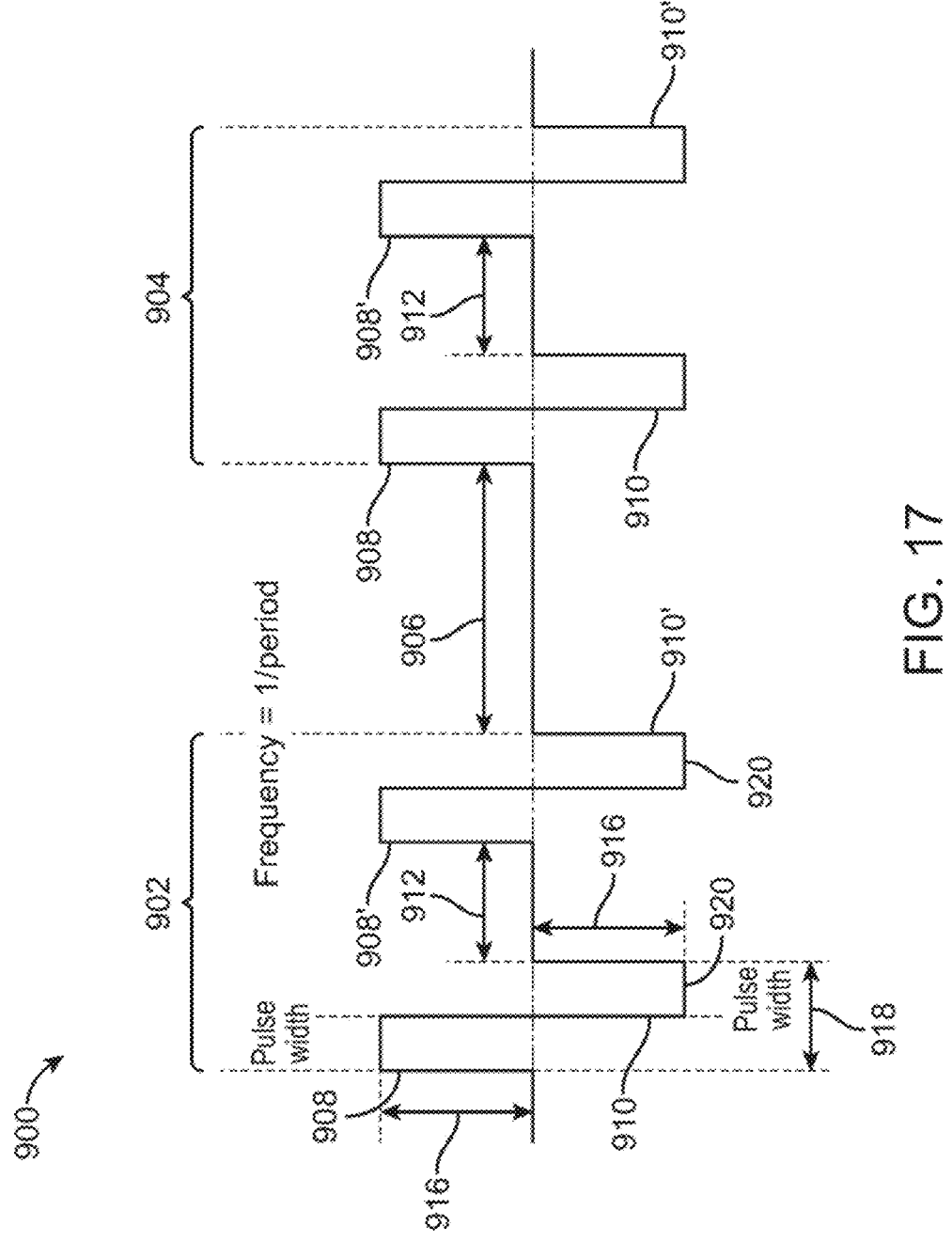
FIG. 17 illustrates an embodiment of a waveform configured for oncological treatments.

In some embodiments, the PEF energy has a waveform and signal parameters configured for oncological treatments, particularly treatment of cancerous tumors. FIG. 17 illustrates an embodiment of such a waveform 900 prescribed by an energy delivery algorithm 152. Here, two packets are shown, a first packet 902 and a second packet 904, wherein the packets 902, 904 are separated by a rest period 906. It may be appreciated that a plurality of packets is typically delivered to the target tissue in the treatment of a tumor. In this embodiment, each packet 902, 904 is comprised of a first biphasic pulse (comprising a first positive peak 908 and a first negative peak 910) and a second biphasic pulse (comprising a second positive peak 908' and a second negative peak 910'). The first and second biphasic pulses are separated by dead time or an inter-cycle delay 912 (i.e., a pause) between each cycle. In some embodiments, the inter-cycle delay 912 is 250 μs-5000 μs, particularly 1000 μs, and in other embodiments the delay 912 is longer such as 2000 μs-5000 μs. In this embodiment, the biphasic pulses are symmetric so that the set voltage 916 is the same for the positive and negative peaks. Here, the biphasic, symmetric waves are also square waves such that the magnitude and time of the positive voltage wave is approximately equal to the magnitude and time of the negative voltage wave. The positive voltage wave causes cellular depolarization in which the normally negatively charged cell briefly turns positive. The negative voltage wave causes cellular hyperpolarization in which the cell potential is negative.

In some embodiments, each high voltage pulse or the set voltage 916 is between about 3000V-6000V, such as 3000V-3300V, 3000V-3500V, 3000V-4000V, 3000V, 3100V, 3200V, 3300V, 3400V, 3500V, 3600V, 3700V, 3800V, 3900V, 4000V, 4100V, 4200V, 4300V, 4400V, 4500V, 4600V, 4700V, 4800V, 4900V, 5000V, 5100V, 5200V, 5300V, 5400V, 5500V, 5600V, 5700V, 5800V, 5900V, 6000V. It may be appreciated that the set voltage 916 may vary depending on whether the energy is delivered in a monopolar or bipolar fashion and such values are particular for monopolar delivery.

The number of pulses per unit of time is the frequency. In some embodiments, the signal has a frequency in the range 100-600 kHz, such as 100-200 kHz, 100-300 kHz, 100-400 Hz, 100-500 kHz, 400-500 kHz, 100 kHz, 200 kHz, 300 kHz, 400 kHz, 500 kHz, 600 kHz. In addition, in some embodiments, cardiac synchronization is utilized to reduce or avoid undesired cardiac muscle stimulation. In some embodiments, biphasic pulses are utilized to reduce undesired muscle stimulation, particularly cardiac muscle stimulation. It may be appreciated that even higher frequencies may be used with components which minimize signal artifacts.

The cycle count 920 is the number of cycles within each packet. Referring to FIG. 17, the first packet 902 has a cycle count 920 of two (i.e. two biphasic pulses). In some embodiments, the cycle count 920 is set between 10-60 cycles per packet, including all values and subranges in between. In some embodiments, the cycle count 920 is 10 cycles, 20 cycles, 30 cycles, 40 cycles, 50 cycles, 60 cycles, 10-20 cycles, 20-30 cycles, 30-40 cycles, 40-50 cycles, 50-60 cycles, including all values and subranges in between. In some embodiments, the on-time per packet is 70-100 μs, including 70 μs, 80 μs, 90 μs, 100 μs. Since a period is the time it takes for a signal to complete an on-and-off cycle, the on-time of a cycle is the time in which the cycle is "on". Likewise, the on-time per packet is the sum of the on-times for the cycles in the packet. The packet duration is the sum of the periods for a packet which is based on the frequency.

In some embodiments, the number of packets delivered during treatment is in the range of 1-1000 packets, typically 20-400 packets or 40-100 packets, including 50 packets, 100 packets, 150 packets, 200 packets, including all values and subranges in between. In some embodiments, the time between packets, referred to as the rest period or inter-packet delay 906, is approximately 3-6 seconds, such as 3 seconds, 4 seconds, 5 seconds, 6 seconds, including all values and subranges in between. In some embodiments the signal is synced with the cardiac rhythm so that each packet is delivered between heartbeats, thus the rest periods coincide with the heartbeats. Thus, the rest period 906 may vary, as the rest period between the packets can be influenced by the cardiac synchronization.

It may be appreciated that the specific settings to desirably alter target tissue are dependent on one another and the electrode design. Therefore, the embodiments provided herein depict specific waveform examples, and it is within the scope of this invention to use multiple waveforms and/or characteristics in any combination to achieve the desired tissue effects.

In some embodiments, the waveform of FIG. 17 induces extravasation and can be used for this purpose in addition to the purpose of treatment. A particular example of such a waveform has a voltage of 1400V, a frequency of 300 kHz, 30 cycles, an on-time of 100 μs, 100 packets, a cycle delay of 1000 μs, and packet delay of 3 seconds. Thus, the overall treatment time in this example is approximately 5 minutes (i.e. 100 packets*3 seconds=300 seconds or approximately 5 minutes). This example will be utilized to illustrate the various timing examples described in later sections.

Sensors

In some embodiments, the energy delivery device 102 includes one or more sensors that can be used to determine pressure, temperature, impedance, resistance, capacitance, conductivity, pH, optical properties (coherence, echogenicity, fluorescence), electrical or light permittivity, and/or conductance, to name a few. In some embodiments, one or more of the electrodes of the energy delivery body 108 act as the one or more sensors. In other embodiments, the one or more sensors are separate from the electrodes. Sensor data can be used to plan the therapy, monitor the therapy and/or provide direct feedback via the processor 154, which can then alter the energy-delivery algorithm 152.

A. Pressure Sensing

It may be appreciated that cells typically respond to mechanical stimuli. One such type of mechanical stimuli is pressure. In general, hydrostatic pressure is determined by the interstitial fluid volume and the general compliance of the targeted tissue interstitium. Important to note that this is variable for tissue types as some organs are encased within a more rigid/less compliant structure (e.g., brain, kidney, etc.), while others are more free to expand/contract (e.g., lungs, muscle, skin, etc.). Increasing hydrostatic pressure can increase permeability of local cell membranes. Thus, it is often beneficial to be mindful of the pressure that the target cells are facing, particularly during local injection of molecules 110. Consequently, in some embodiments, the energy delivery device 102 includes a pressure sensor. Pressure sensor measurements may be utilized to monitor edema levels resulting from extravasation, such as before, during and/or after injection of molecules 110 and treatment energy. Thus, inducement of extravasation can be adjusted to reach desired edema levels at particular times throughout a treatment protocol.

Figures 18A, 18B:
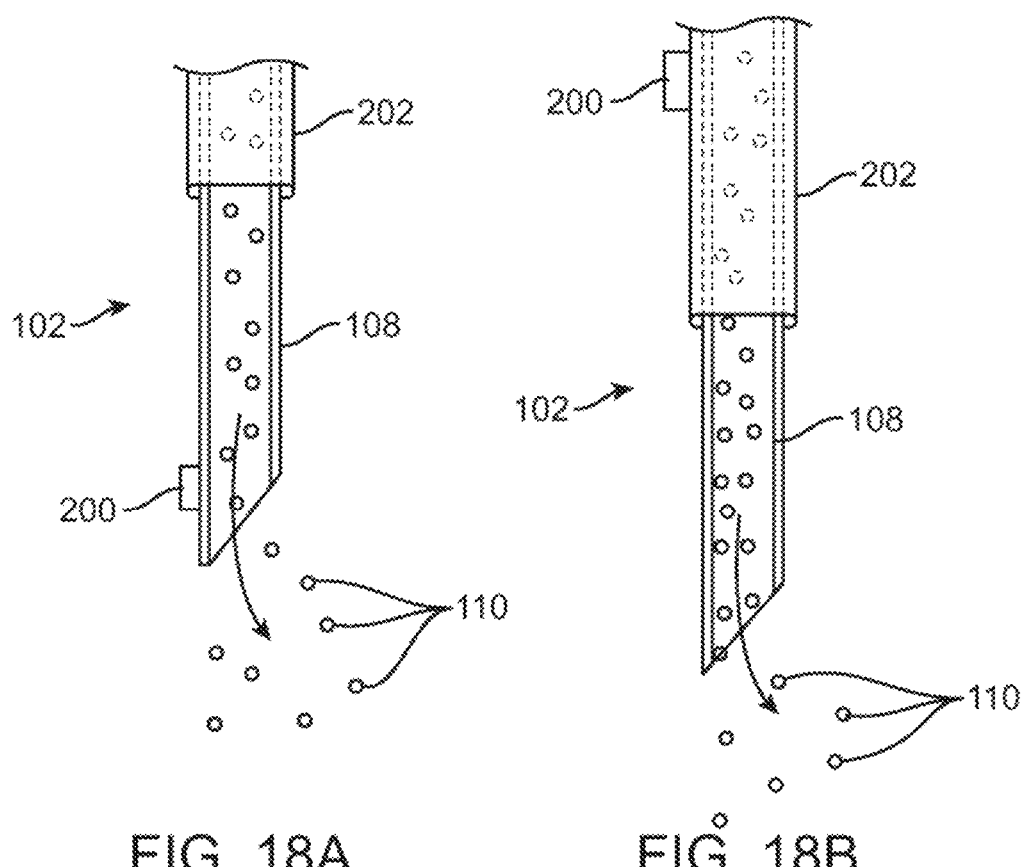
FIGS. 18A-18C illustrate embodiments of a pressure sensor.

A variety of pressure sensors 200 may be used. In some embodiments, the pressure sensor 200 is disposed along a distal tip of the energy delivery device 102, such as illustrated in FIG. 18A. Here, the energy delivery device 102 comprises an energy delivery body 108 having a needle shape, wherein the energy delivery body 108 is at least partially covered by an insulative sleeve 202. As illustrated, molecules 110 are passed through the energy delivery body 108 to the nearby target tissue area. This allows the pressure sensor 200 to monitor the pressure during the injection of the molecules 110 and application of treatment energy. In other embodiments, the pressure sensor 200 is disposed along the distal end of the energy delivery device 102 but proximal to the tip, such as illustrated in FIG. 18B. Here, the pressure sensor 200 is disposed along the insulative sleeve 202 that at least partially covers the energy delivery body 108. Having a relative pressure measurement at the tissue level allows the user to understand the distribution of the injected molecules 110 within the tissue. Considering the injected solution at a known pressure and flow rate (values able to be easily measured near the proximal end of the device 102), an additional relative measurement at the distal end will provide the information to understand the spatial distribution of the molecules along the target tissue as well as the temporal pressure profile.

In some embodiments, the pressure sensor 200 comprises a strain-gauge transducer. Strain-gauge transducers are typically characterized by exhibiting a change in their form of output in response to the measurand (i.e., strain, electrical resistance, or wavelength). Sensitivity is determined by the relative change of resistance with respect to length.

In other embodiments, the pressure sensor 200 comprises a diaphragm displacement sensor. Diaphragm displacement sensors are based on micro-electromechanical systems technology, in which the sensors have a bendable flat surface (diaphragm) over a sealed cavity. The diaphragm bends or deforms in response to the change in pressure. The resultant form of output can be capacitance based or piezoelectric transducer based. In some embodiments, a sensor 200 is placed at the distal tip of the energy delivery device 102, while its corresponding diaphragm is disposed proximal to the sensor 200, thus enabling a measurement of the pressure drop across the distance therebetween. In instances where such placement of a sensor is difficult, such as due to size restrictions, a pressure sensing optical fiber may be preferred.

Figure 18C:
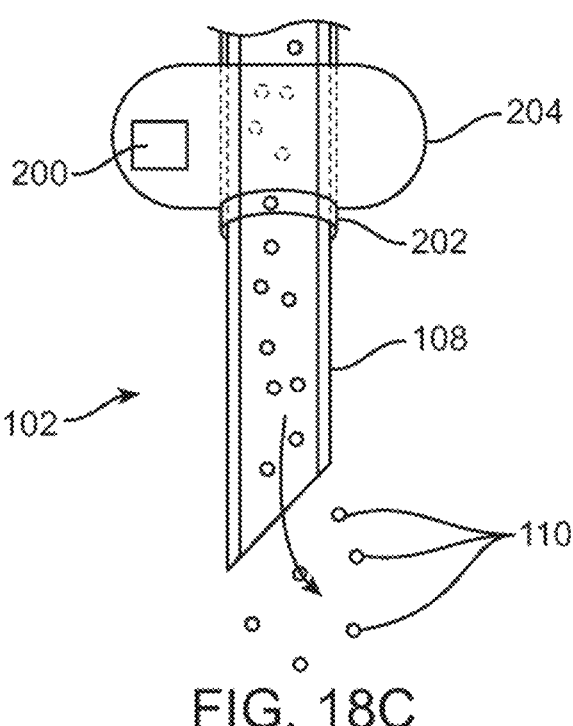

In some embodiments, the energy delivery device 102 includes an expandable member 204 disposed along its distal end, such as illustrated in FIG. 18C. Here, the expandable member 204 is mounted on an insulative sleeve 202 that at least partially covers the energy delivery body 108 having a needle shape. Such positioning of the expandable member 204 can assist in preventing reflow of the solution of molecules 110 back up the pathway created by inserting the energy delivery device 102. This may improve the pressure distribution within the target tissue and therefore overall delivery of the molecules 110. The expandable member 204 may also prevent movement of the needle-like energy delivery body 108 during delivery of the PEF energy. In some embodiments, a pressure sensor 200 mounted on the expandable member 204 monitors the pressure within the expandable member 204. This ensures proper inflation of the expandable member 204. Further, in some embodiments, the pressure sensor 200 monitors tissue pressure during infusion of molecules 110 and/or PEF energy delivery.

Timing Embodiments

Figure 19:
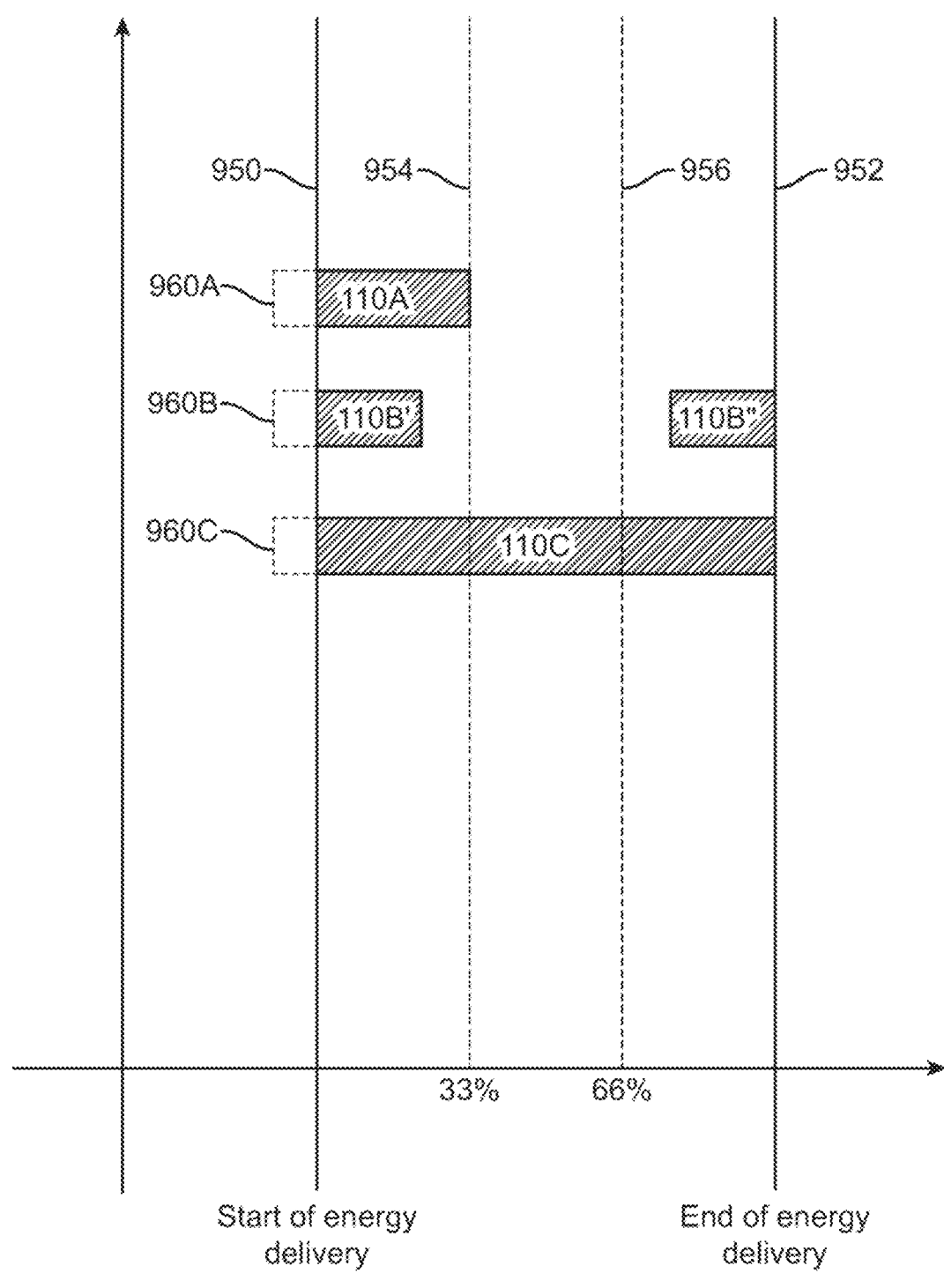
FIG. 19 illustrates three example timing embodiments for molecule delivery in relation to a treatment delivery.

It may be appreciated that the timing of the PEF energy delivery and the molecule 110 delivery may be optimized for improved outcomes, such as improved treatment of abnormal tissue such as a tumor. FIG. 19 illustrates three example timing embodiments for molecule 110 delivery in relation to a treatment delivery. Here, the x-axis illustrates the timing of the PEF energy delivery; particular demarcations include the start of a PEF energy delivery 950 protocol and the end of the PEF energy delivery 952 protocol. Such a protocol is considered sufficient to treat a target tissue area, such as to treat a tumor such as by killing all or a desired amount of the tumor. The waveform described above (i.e. having a voltage of 1400V, a frequency of 300 kHz, 30 cycles, an on-time of 100 μs, 100 packets, a cycle delay of 1000 μs, and packet delay of 3 seconds) will be used for illustration purposes. In this example, the time between the start and end of the treatment is approximately 5 minutes. Additional demarcations are provided, such as a demarcation 954 at approximately ⅓ (33%) of the way through the treatment and a demarcation 956 at approximately ⅔ (66%) of the way through the treatment.

In the first example, molecules 110A are delivered near the start of the PEF energy delivery 950 and are continued to be delivered through a first portion of the PEF energy delivery, such as through the first 25-33% of the PEF energy delivery. In this example, the molecules 110A are delivered for approximately 1.25-1.67 minutes. It may be appreciated that in some instances the molecules 110A are additionally delivered prior to the start of the PEF energy delivery 950 (as indicated by dashed line 960A) to ensure that the molecules 110A have arrived at the target tissue by the time the PEF energy delivery has begun. In some embodiments, the molecules 110A are delivered 10 seconds to 10 minutes prior to delivery of PEF energy, typically 1 minute to 10 minutes prior to delivery of PEF energy. It may be appreciated that the molecules 110A may be delivered by the various methods described herein, including local injection, regional delivery and systemic delivery, such as intravenous delivery. Delivery methods such as systemic delivery may benefit from starting earlier than local delivery given the dynamics. It may be appreciated that a significant portion of the treatment effect (e.g. extravasation and ablation) typically occurs within the first 25-33% of the treatment time while the remaining PEF energy delivery helps reinforce the effect. Thus, aligning the molecule 110A delivery with this period allows the molecules 110A to be available during this valuable time, thereby maximizing their effect.

In the second example, molecules 110B' are delivered near the start of the PEF energy delivery 950 and are continuously delivered through a first portion of the PEF energy delivery, such as through the first 25% of the PEF energy delivery. An additional delivery of molecules 110B" is provided before the end of the PEF energy delivery 950, such as to be delivered over the last 25% of the PEF energy delivery period. Thus, in this example, the molecules 110B' are delivered for approximately 1.25 minutes near the start of PEF energy delivery, are not delivered for 2.50 minutes and the molecules 110B" are then delivered for approximately 1.25 minutes to the end of the PEF energy delivery 952. Again, it may be appreciated that in some instances the molecules 110B' are additionally delivered prior to the start of the PEF energy delivery 950 (as indicated by dashed line 960B) to ensure that the molecules 110B' have arrived at the target tissue by the time the PEF energy delivery has begun. It may be appreciated that the molecules 110B', 110B" may be delivered by the various methods described herein, including local injection, regional delivery and systemic delivery, such as intravenous delivery. Delivery methods such as systemic delivery may benefit from starting earlier than local delivery given the dynamics. Again, it may be appreciated that a significant portion of the treatment effect (e.g. extravasation and ablation) typically occurs within the first 25-33% of the treatment time while the remaining delivery helps reinforce the effect. Thus, aligning the molecule delivery with this period combines allows the molecules to be available during this valuable time, thereby maximizing their effect. In addition, the delivery of molecules 110B" over a later portion of the PEF energy delivery period enhances reinforcement of the effect, such as a final push of molecules post extravasation allowing more of the molecules 110B" to settle within the treatment area.

In the third example, molecules 110C are delivered near the start of the PEF energy delivery 950 and are continuously delivered through the PEF energy delivery period to the end of the PEF energy delivery period 952. Thus, in this example, the molecules 110C are delivered for approximately 5 minutes over the duration of the PEF energy delivery period. Again, it may be appreciated that in some instances the molecules 110C are additionally delivered prior to the start of the PEF energy delivery 950 (as indicated by dashed line 960C) to ensure that the molecules 110C have arrived at the target tissue by the time the PEF energy delivery has begun. It may be appreciated that the molecules 110C may be delivered by the various methods described herein, including local injection, regional delivery and systemic delivery, such as intravenous delivery. Delivery methods such as systemic delivery may benefit from starting earlier than local delivery given the dynamics. Such continuous delivery of molecules 110C, such as at a constant infusion rate, maximizes the coordinated interaction of the molecules, extravasation and ablation throughout the treatment. In some instances, this combination yields the strongest results. A slow and constant delivery of molecules 110C over the course of the 5-minute PEF energy delivery allows for more molecules 110C to slowly diffuse across tissue with the added benefit of shockwave-like mechanical force being emitted from the energy delivery device with delivery of every packet of PEF energy.

Figure 20:
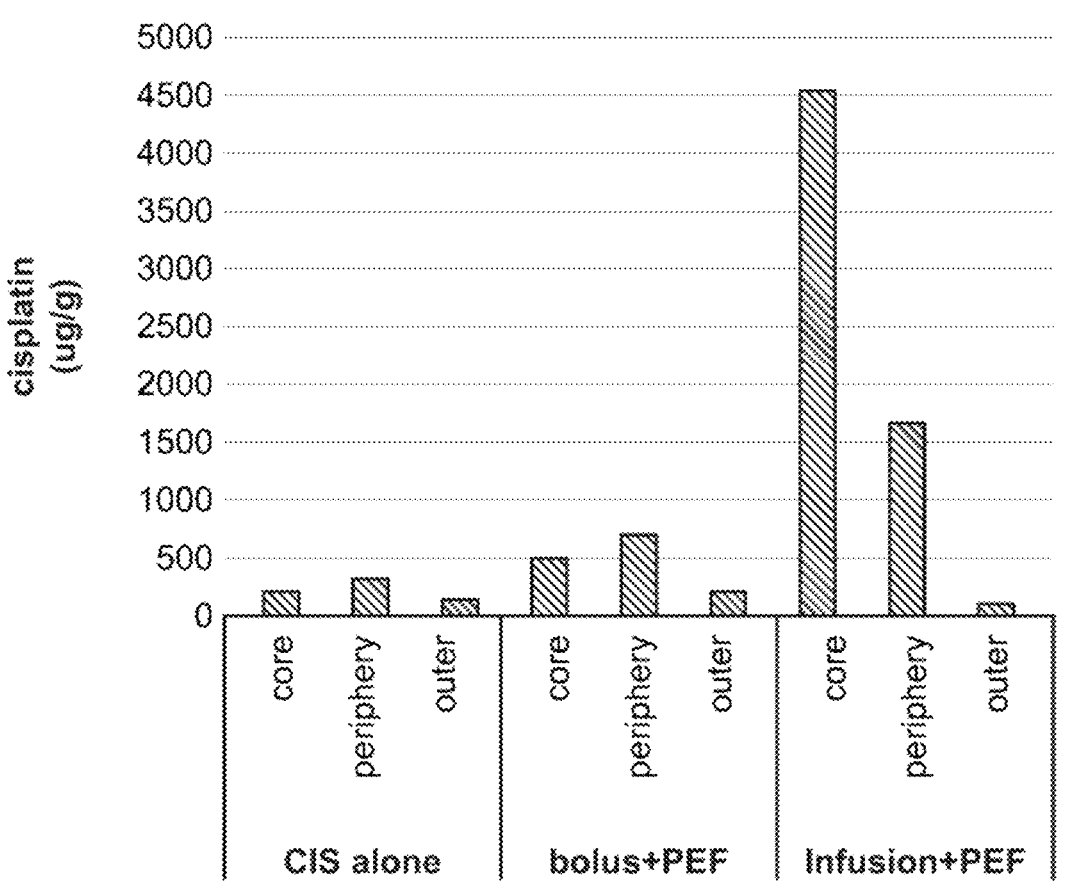
FIG. 20 provides results of a laboratory study.

FIG. 20 provides results of a laboratory study illustrating this phenomenon. In this study, a pig was anesthetized prior to performing a laparotomy to expose the liver. Cisplatin (0.1 mg) was injected in the pig liver and combined with PEF energy delivery using three modalities: 1) local injection of cisplatin without delivery of PEF energy (CIS alone group), 2) cisplatin was injected in a different area of pig liver and PEF was delivered in the same location 2 minutes after the bolus of the drug (bolus+PEF group), 3) cisplatin was delivered over the course of 5 minutes concomitantly with the delivery of PEF (infusion+PEF group). The liver was collected 2 hours after PEF delivery and the treated areas were sectioned to separate the core, the periphery and the outer periphery. To select in the treated areas of the core, a 6 mm punch biopsy was used. To collect in the periphery, a 10 mm punch biopsy was used. And, to isolate the outer periphery, a 15 mm punch biopsy was used. The liver samples were analyzed by mass spectrometry (ICP-MS) to quantify the concentration of cisplatin. As shown in FIG. 20, the highest concentration of cisplatin, both in the core and periphery, was achieved when the drug and PEF energy were delivered simultaneously (infusion+PEF group), particularly wherein the drug was delivered throughout treatment with PEF energy.

It may be appreciated that although the above timing examples of FIG. 19 are provided in terms of treatment time, relative timing of delivery of molecules and PEF energy may be controlled based on other factors such as volume of molecules 110 to be delivered and/or delivery/flow rates. For example, in some embodiments, a predetermined volume of molecules 110 is delivered to the target tissue area throughout delivery of PEF energy during a treatment protocol. Thus, the rate in which it is delivered is based on the total volume of molecules to be delivered and the predetermined treatment time. In other embodiments, a predetermined volume of molecules is delivered during a first portion of the energy delivery, such as the first 25-33% of energy delivery, and then no molecules are delivered for the remainder of the treatment. In other embodiments, half of a predetermined volume of molecules is delivered during a first portion of energy delivery, such as the first 25% of energy delivery, and half of the predetermined volume is delivered during a second portion of the energy delivery, such as the last 25% of energy delivery. In each of these scenarios, the delivery rate is based on a particular volume of molecules and a particular amount of treatment time. It can be inferred that the molecules would be delivered with the slowest flow rate in the example wherein the molecules were delivered throughout the entire treatment protocol. Likewise, the fastest flow rate would occur in the example wherein the molecules were delivered over the first 25-33% of the energy delivery and then not delivered for the remainder of the treatment.

In some embodiments, a user manually delivers the molecules (e.g. by local injection, regional injection, systemic infusion, etc.) and activates the generator to deliver the PEF energy (e.g. by footswitch). In such embodiments, timing and coordination is achieved by the user alone or with the assistance of various components, such as timers, sensors, alerts, data feedback, etc.

In other embodiments, the PEF energy is delivered in response to one or more components, such as one or more sensors, one or more timers, one or more monitors, a combination, etc. In some embodiments, a controller is provided that is configured to control delivery of the pulsed electric field energy in response to the one or more components. Example controllers include a switch box, a delivery control board, a relay system, a dispatch unit, a microcontroller, a molecular distribution control board, a molecule control system, a fluid control system, a fluid control valve, a molecular fluid servosystem, to name a few. The controller may be included in or separate from the generator and functions in conjunction with the generator so as to control the PEF energy delivery. In some embodiments, the controller utilizes one or more components wherein the one or more components comprises a sensor that senses a flow rate of molecules being delivered to the patient. In other embodiments, the controller utilizes one or more components wherein the one or more components comprises a sensor that senses pressure of a syringe pump configured to deliver molecules to the patient. In other embodiments, the controller utilizes one or more components wherein the one or more components comprises a timer and wherein the controller causes delivery of the pulsed electric field energy at a predetermined time after commencement of delivery of molecules to the target tissue area.

As related to the examples herein above, in some embodiments the controller causes delivery of the pulsed electric field energy throughout delivery of molecules to the target tissue area. In the embodiment wherein a predetermined volume of molecules is delivered during a first portion of the energy delivery, such as the first 25-33% of energy delivery, and then no molecules are delivered for the remainder of the treatment, the controller may cause delivery of the pulsed electric field energy throughout delivery of molecules to the target tissue area and then continue delivery of the pulsed electric field energy for a period 200-300% longer than the delivery of molecules. In the embodiment wherein half of a predetermined volume of molecules is delivered during a first portion, such as the first 25% of energy delivery, and half of the predetermined volume is delivered during a later portion, such as the last 25% of energy delivery, the controller may cause delivery of the pulsed electric field energy throughout an additional delivery of molecules that occurs at a time period after the initial delivery of molecules.

It may be appreciated that in some embodiments the PEF energy and the molecules 110 are delivered by separate devices and in other embodiments the PEF energy and the molecules 110 are delivered by the same device. Thus, in some embodiments, the energy delivery device 102 is configured to deliver energy to a target tissue area and configured to deliver a plurality of molecules to the target tissue area. In such embodiments, the energy may be delivered through an energy delivery body 108 and the molecules 110 may be delivered through a lumen and a port near the distal end of the device 102. In some embodiments, the molecules 110 are stored in a reservoir, pump or syringe separate from the device 102 and connectable with the lumen, and in other embodiments the molecules 110 are stored in a reservoir within the device 102 connected with the lumen or directly to the port.

Alternative Device Designs

The energy may be delivered by a variety of energy delivery devices 102. Typically, the energy delivery device 102 comprises a flexible elongate shaft having a distal end, capable of being advanced to the target tissue within the body, and an energy delivery body 108 disposed near the distal end. The energy delivery body 108 comprises one or more electrodes that delivers the energy to the target tissue.

In some embodiments, the molecules 110 and the energy are delivered by the energy delivery device 102. This is in contrast to system delivery of the molecules 110 described and illustrated in relation to FIGS. 5A-5C. In this instance, the induced extravasation may create an improved (e.g. more uniform) distribution of the molecules throughout the target treatment area and/or trap the molecules 110 in the target tissue area so that the molecules are at least temporarily resisted from diluting away.

Figures 21A, 21B:
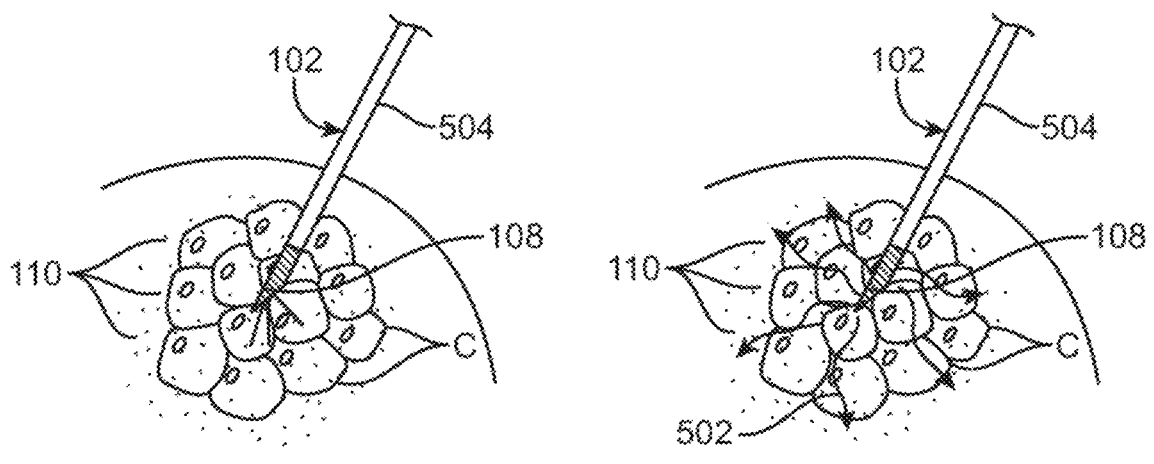
FIGS. 21A-21B illustrate molecules and energy is delivered locally from an energy delivery device.

FIGS. 21A-21B illustrate an energy delivery device 102 having an energy delivery body 108 having a needle shape. The tip of the needle shape is able to penetrate similarly to a needle and deliver molecules 110 through its internal lumen. In addition, the energy delivery body 108 is electrically insulated with an insulation layer 504 except for the tip of the needle shape which acts as an electrode. FIG. 21A illustrates direct injection of molecules 110 to a target tissue through the energy delivery body 108. Again, the target tissue is illustrated as cells C (not to scale). The tip is inserted in or near the target tissue so that the injected molecules 110 are able to bathe the target tissue and optionally dwells for biodistribution. Referring to FIG. 21B, PEF energy is then delivered to the target tissue from the energy delivery body 108 as indicated by wavy lines 502. When the PEF energy is conditioning PEF, the result is local edema. When the PEF energy is therapeutic PEF, the energy assists in uptake of the molecules 110 into the cells C or influences the effect of the molecules 110 on the cells.

Figure 22:
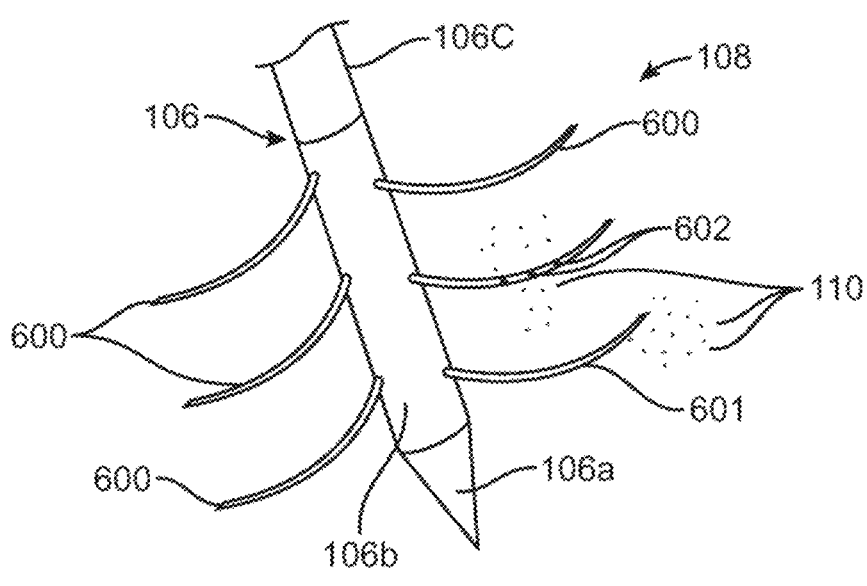
FIG. 22 illustrates an energy delivery device comprising a shaft having an energy delivery body near its distal end, wherein the energy delivery body comprises a plurality of tines.

FIG. 22 illustrates an energy delivery device 102 comprising a shaft 106 having an energy delivery body 108 near its distal end, wherein the energy delivery body 108 comprises a plurality of tines 600. Typically, the tines 600 have a pointed shape so as to penetrate tissue. Likewise, the tines 600 typically extend laterally outward from the shaft 106, and in some embodiments the tines 600 are disposed circumferentially around the shaft 106. It may be appreciated that in some embodiments, the tines 600 are disposed on a side of the shaft 106, such aligned in a row. In some embodiments, the tines 600 extend the same distance from the shaft 106 and in other embodiments the tines 600 extend a varied distance. It may be appreciated that in some embodiments, the extension of at least some of the tines 600 from the shaft 106 is adjustable.

Typically, each time 600 delivers molecules 110 and/or energy therefrom. In some embodiments, molecules 110 are delivered from the tip 601 of the tine 600 and in other embodiments molecules 110 are delivered from delivery ports 602 along the tine 600. In some embodiments, the tines 600 are energizable together (so as to act as a single electrode) or at least some of the tines 600 are individually energizable (so as to act in bipolar pairs).

In this embodiment, the shaft 106 has three sections, a first section 106a, a second section 106b and a third section 106c. As illustrated in FIG. 22, the first section 106a is distal to the second section 106b which is distal to the third section 106c. Each section 106a, 106b, 106c may be insulated or non-insulated so as to create a variety of different electrode combinations. This may allow various electric field shapes and/or direct the electric field in desired directions. It may also be appreciated that in some embodiments, at least a portion of at least one tine 600 is insulated so as to direct the energy emanating therefrom. Overall, the tines 600 are often able to deliver molecules 110 and/or energy to a larger volume of target tissue with a single placement of the energy delivery device 102 than with a device 102 having an energy delivery device 108 comprising a single needle.

Figure 23:
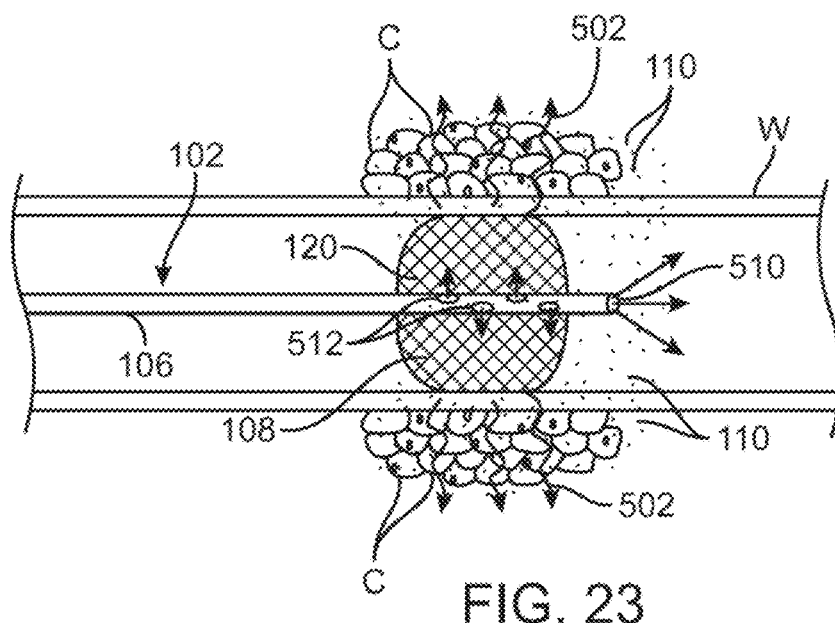
FIG. 23 illustrates an energy delivery device comprising an energy delivery body having a basket shape configured for treating target tissue endoluminally.

FIG. 23 illustrates an energy delivery device 102 comprising an energy delivery body 108 having a basket shape configured for treating target tissue endoluminally. Here the target tissue comprises cells C disposed near a wall W of a body lumen, particularly wrapping at least partially circumferentially around the body lumen. In this embodiment, the energy delivery body 108 is comprised of a plurality of wires or ribbons 120 forming a spiral-shaped basket serving as an electrode. In some embodiments, the energy delivery body 108 is self-expandable and delivered to a targeted area in a collapsed configuration. This collapsed configuration can be achieved, for example, by placing a sheath over the energy delivery body 108. Retraction of the sheath or advancement of the energy delivery body 108 from the sheath allows the energy delivery body 108 to self-expand. In other embodiments, the energy delivery device 102 includes a handle having an energy delivery body manipulation knob wherein movement of the knob causes expansion or retraction/collapse of the basket-shaped electrode. The basket-shaped electrode is expandable within a body lumen or passageway (naturally occurring or created within the body) so as to contact at least a portion of the wall W of the lumen. Molecules 110 are delivered from the energy delivery device 102, such as through a distal end port 510 and/or through various side ports 512 along a shaft 106 of the device 102, such as within the basket-shaped electrode, as illustrated in FIG. 23. The molecules 110 are able to bathe the target tissue and optionally dwell for biodistribution. Conditioning PEF energy is delivered to the target tissue from the energy delivery body 108 as indicated by wavy lines 502. This causes induced extravasation in the local area surrounding the lumen. Therapeutic PEF energy assists in uptake of the molecules 110 into the cells C or influences the effect of the molecules 110 on the cells.

Figure 24:
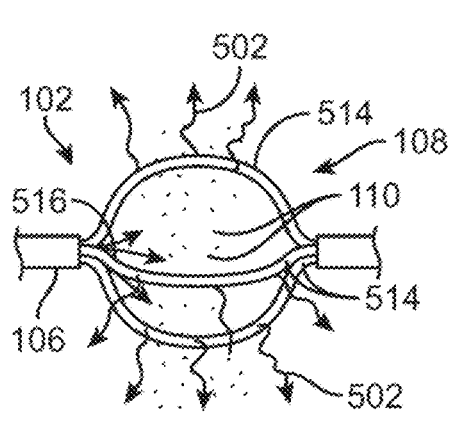
FIG. 24 illustrates another embodiment of an energy delivery device comprising an energy delivery body having a shape configured for treating target tissue endoluminally, wherein the energy delivery body comprises at least two protrusions, each protrusion extending radially outwardly so as to contact an inner luminal wall.

FIG. 24 illustrates another embodiment of an energy delivery device 102 comprising an energy delivery body 108 having a shape configured for treating target tissue endoluminally. In this embodiment, the energy delivery body 108 comprises at least two protrusions 514, each protrusion extending radially outwardly so as to contact an inner luminal wall W. It may be appreciated that although a single protrusion may be present, typically two protrusions are present to apply substantially opposing forces to the walls the lumen. In the embodiment of FIG. 24, three protrusions 514 are present. In some embodiments, each protrusion 514 is formed by a wire or ribbon which acts as an electrode and bends or bows radially outward from the longitudinal axis or shaft 106 of the delivery device 102. In this embodiment, the protrusions 514 together act as a single electrode. However, in other embodiments, one or more protrusions 514 are independently energizeable so as to act as multiple electrodes (e.g. as one or more bipolar pairs). The protrusions 514 may be comprised of a variety of suitable materials so as to act as an electrode, such as stainless steel, spring steel, or other alloys, and may be, for example, round wires or ribbon. In some embodiments, a portion of the protrusions 514 are insulated with a segment of insulation, such as a polymer (e.g., PET, polyether block amide, polyimide). For example, in some embodiments at least a portion of the proximal and distal ends of the energy delivery body 108 are insulated to direct the energy laterally, toward the walls W.

In some embodiments, the energy delivery body 108 of FIG. 24 is self-expandable and delivered to a targeted area in a collapsed configuration. The protrusions bow outwardly during expansion within a body lumen or passageway (naturally occurring or created within the body) so as to contact at least a portion of the wall W of the lumen. Molecules 110 is delivered from the energy delivery device 102, such as through a port 516 within the energy delivery body 108, as illustrated in FIG. 24. The molecules 110 are able to bathe the target tissue and optionally dwell for biodistribution. PEF energy is then delivered to the target tissue from the energy delivery body 108 as indicated by wavy lines 502. The PEF energy delivers the molecules 110 into the cells C.

Figure 25:
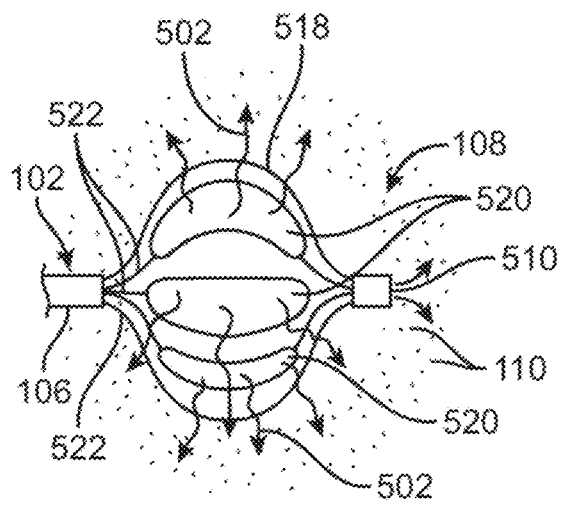
FIG. 25 illustrates another embodiment of an energy delivery device comprising an energy delivery body having a shape configured for treating target tissue endoluminally, wherein the energy delivery body comprises an expandable member, such as an inflatable balloon, having an electrode mounted thereon or incorporated therein.

FIG. 25 illustrates another embodiment of an energy delivery device 102 comprising an energy delivery body 108 having a shape configured for treating target tissue endoluminally. In this embodiment, the energy delivery body 108 comprises an expandable member 518, such as an inflatable balloon, having an electrode 520 mounted thereon or incorporated therein. The energy delivery body 108 is delivered to a targeted area in a collapsed configuration. In this embodiment, the electrode 520 has the form of a pad having a relatively broad surface area and thin cross-section. The pad shape provides a broader surface area than other shapes, such as a wire shape. Each electrode 520 is connected with a conduction wire 522 which electrically connects the electrode 520 with the generator. In this embodiment, the three electrodes 520 are visible, however it may be appreciated that additional electrodes may be present around the expandable member 518. It may be appreciated that any number of electrodes 520 may be present, acting as a single electrode or acting independently or in combination. Placement of the electrodes 520 and/or selective energizing of the electrodes 520 may direct the energy toward particular target locations. In some embodiments, the electrodes 520 are comprised of flexible circuit pads or other materials attached to the expandable member 518 or formed into the expandable member 518. In some embodiments, the electrodes 520 are distributed radially around the circumference of the expandable member 518 and/or distributed longitudinally along the length of the expandable member 518. Such designs may facilitate improved deployment and retraction qualities, easing user operation and compatibility with introducer lumens.

Upon expansion of the expandable member, one or more of the electrodes 520 are positioned so as to contact at least a portion of the wall W of the lumen. Molecules 110 are delivered from the energy delivery device 102, such as through a distal end port 510, as illustrated in FIG. 25. The molecules 110 are able to bathe the target tissue and optionally dwell for biodistribution. Conditioning PEF energy is delivered to the target tissue from the energy delivery body 108 as indicated by wavy lines 502. This causes induced edema in the local area surrounding the lumen. Therapeutic PEF energy assists in uptake of the molecules 110 into the cells C or influences the effect of the molecules 110 on the cells.

Figure 26:
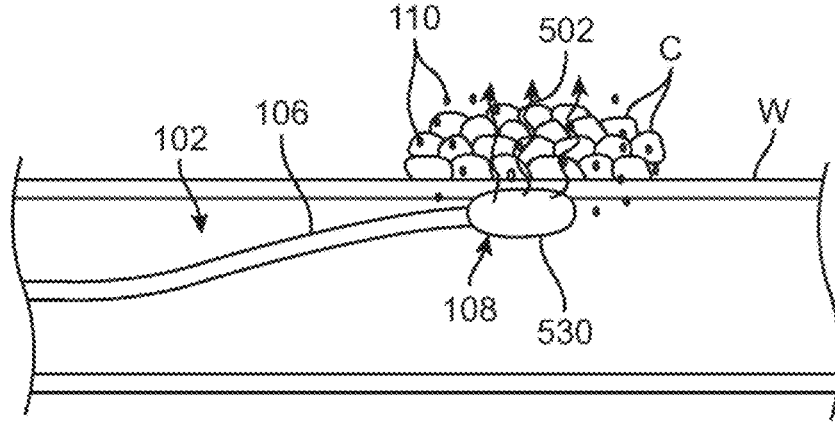
FIG. 26 illustrates an embodiment of an energy delivery device wherein the delivery body has a finger-tip shape configured to contact an inner lumen wall.

FIG. 26 illustrates another embodiment of an energy delivery device 102. Here the energy delivery body 108 has a finger-tip shape configured to contact an inner lumen wall W. In this embodiment, the energy delivery device 102 has an elongate shaft 106 and finger-tip electrode 530 disposed at its distal tip. The finger-tip electrode 530 is positionable against the portion of the lumen wall W near the target tissue cells C. The molecules 110 may be delivered by any suitable method, such as systemically, regionally or locally, such as by injection through a separate device or through the energy delivery device 102. FIG. 26 illustrates delivery of molecules 110 through the finger tip electrode 530. Conditioning PEF energy is delivered to the target tissue from the finger tip electrode 530 as indicated by wavy lines 502. This causes induced extravasation in the local area surrounding the lumen. Therapeutic PEF energy assists in uptake of the molecules 110 into the cells C or influences the effect of the molecules 110 on the cells.

It may be appreciated that in some embodiments, PEF energy is delivered to a conductive fluid (e.g. blood, saline, etc.) in contact with the target tissue. Thus, the energy is able to pass through the conductive fluid to the target tissue for delivery. In other embodiments, delivery of energy to the conductive fluid promotes delivery of molecules into the cells of the fluid itself, such as delivery into leukocytes in blood.

It may be appreciated that although a variety of embodiments described herein include multiple steps or methodologies, such as extravasation, molecule delivery, transfection, ablation, etc., each may be utilized alone or in any combination with any other method. For example, extravasation may be induced for a variety of purposes with or without follow-on therapy. It may be appreciated that PEF energy may be utilized to improve diffusion and distribution of molecules amongst tissue for a variety of therapies, many of which do not involve ablation or further therapy. For example, when delivering agents via inhalation, PEF energy may be delivered before, during or after inhalation to cause the agents to reach deeper cells within the lung anatomy, such as smooth muscle cells, cartilage, etc. Likewise, when anti-epilepsy drugs are delivered by IV, local injection or via the cerebrospinal fluid, PEF energy may be delivered to cause better distribution of the drug amongst the foci of where the seizures are starting. These are just a few examples of improved delivery of an agent to treat a condition or disease.

Likewise, a variety of therapies and combinations of therapies may be provided to a patient without extravasation induction. Further, certain effects of portions of the therapy may still ensue regardless of the presence of particular steps in the therapy. Likewise, a variety of treatment aspects described herein may ensue without the inclusion of all of the steps of the methodology. For example, steps ensuing after the creation of a debris field DF (FIGS. 8A-8B) would occur regardless of the use of induced extravasation in the procedure. Thus, clearing of the debris field DF and the resultant immune response, including the effect on any metastases, would occur regardless of the use of induced extravasation. However, the induced extravasation may affect the extent of these effects, such as by improving the size, depth, components, etc., of the debris field.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

We claim:

1. A system for treating a target tissue area of a patient comprising:

an energy delivery device having at least one energy delivery body configured to be positioned near the target tissue area within the patient; and a generator in electrical communication with the at least one energy delivery body, wherein the generator includes at least one energy delivery algorithm configured to provide an electric signal of pulsed electric field energy deliverable to the at least one energy delivery body so as to induce extravasation of fluid from vasculature near or within the target tissue area.

2. A system as in claim 1, wherein the induced extravasation is sufficient to bias molecules delivered to the target tissue area toward entry to cells of the target tissue area.

3. A system as in claim 2, wherein the molecules comprise drugs, chemotherapy drugs, immunotherapy drugs, and/or monoclonal antibodies.

4. A system as in claim 2, wherein the molecules include auxiliary materials including polymeric nanoparticles, liposomes, PEGylated liposomes, lipofectamine, cell-penetrating peptides (CPC), dimethyl sulfoxide (DMSO), cholesterol, or other materials known to interact with cell membrane fluidity and mechanics.

5. A system as in claim 2, wherein the energy delivery device is configured to deliver the molecules to the target tissue area of the patient.

6. A system as in claim 1, wherein the extravasation delivers molecules from the vasculature near or within the target tissue area to interstitial spaces around cells within the target tissue area.

7. A system as in claim 1, further comprising a controller that is configured to control delivery of the pulsed electric field energy in response to at least one component.

8. A system as in claim 7, wherein the at least one component comprises a sensor that senses a flow rate of molecules being delivered to the patient.

9. A system as in claim 7, wherein the at least one component comprises a sensor that senses pressure of a syringe pump configured to deliver molecules to the patient.

10. A system as in claim 7, wherein the at least one component comprises a timer and wherein the controller causes delivery of the pulsed electric field energy at a predetermined time after commencement of delivery of molecules to the target tissue area.

11. A system as in claim 7, wherein the controller causes delivery of the pulsed electric field energy throughout delivery of molecules to the target tissue area.

12. A system as in claim 7, wherein the controller causes delivery of the pulsed electric field energy throughout delivery of molecules to the target tissue area and continues 200-300% longer than the delivery of molecules.

13. A system as in claim 7, wherein the controller causes delivery of the pulsed electric field energy throughout an additional delivery of molecules that occurs at a time period after the delivery of molecules.

14. A system as in claim 1, wherein the electric signal of pulsed electric field energy deliverable to the at least one energy delivery body so as to induce extravasation within the target tissue area also causes cell death within the target tissue area.

15. A system as in claim 14, wherein the signal comprises at least two packets of biphasic pulses separated by an inter-packet delay.

16. A system as in claim 1, wherein the target tissue area comprises at least a portion of a tumor or an abnormal growth.

17. A system for treating a target tissue area of a patient comprising:

an energy delivery device configured to deliver energy to the target tissue area and configured to deliver a plurality of molecules to the target tissue area; and a generator in electrical communication with the energy delivery device, wherein the generator includes at least one energy delivery algorithm configured to provide an electric signal of pulsed electric field energy deliverable to the at least one energy delivery body that induces extravasation of fluid from vasculature near or within the target tissue area wherein the extravasation is sufficient to bias molecules delivered to the target tissue area toward entry to cells of the target tissue area.

18. A system as in claim 17, further comprising a controller that coordinates delivery of the pulsed electric field energy and the delivery of the plurality of molecules.

19. A system as in claim 18, wherein the controller causes commencement of the delivery of the pulsed electric field energy at a predetermined time after commencement of delivery of the plurality of molecules.

20. A system as in claim 18, wherein the controller causes simultaneous delivery of the pulsed electric field energy and delivery of molecules to the target tissue area throughout a treatment of the target tissue area.

21. A system as in claim 18, wherein the controller causes delivery of the pulsed electric field energy throughout an additional delivery of molecules that occurs at a time period after the delivery of molecules.

22. A system as claim 17, wherein the electric signal of pulsed electric field energy deliverable to the at least one energy delivery body so as to induce extravasation near or within the target tissue area also causes cell death within the target tissue area.

23. A system as in claim 22, wherein the signal comprises at least two packets of biphasic pulses separated by an inter-packet delay.

24. A system as in claim 17, wherein the generator further includes at least one additional energy delivery algorithm configured to provide an additional electric signal of pulsed electric field energy deliverable to the at least one energy delivery body so as to cause cell death within the target tissue area.

25. A system as in claim 24, wherein the additional electric signal is comprised of a plurality of pulses forming a packet, wherein each of the plurality of pulses has a duration of 0.5-200 μs, and wherein the packet has a cumulative on-time of 1-200 μs.

26. A system as in claim 24, wherein the additional electric signal comprises 40-100 packets.

* * * * *